United States Patent
Greenhalgh et al.

(10) Patent No.: US 12,070,380 B2
(45) Date of Patent: *Aug. 27, 2024

(54) HERNIA REPAIR GRAFTS HAVING ANTI-ADHESION BARRIERS

(71) Applicant: TELA Bio, Inc., Malvern, PA (US)

(72) Inventors: Skott Greenhalgh, Gladwyne, PA (US); John-Paul Romano, Chalfont, PA (US); Travis Speicher, Newtown Square, PA (US)

(73) Assignee: TELA Bio, Inc., Malvern, PA (US)

( * ) Notice: Subject to any disclaimer, the term of this patent is extended or adjusted under 35 U.S.C. 154(b) by 139 days.

This patent is subject to a terminal disclaimer.

(21) Appl. No.: 17/938,250

(22) Filed: Oct. 5, 2022

(65) Prior Publication Data

US 2023/0277287 A1    Sep. 7, 2023

Related U.S. Application Data

(63) Continuation of application No. 16/792,068, filed on Feb. 14, 2020, now Pat. No. 11,464,616, which is a
(Continued)

(51) Int. Cl.
*A61F 2/00* (2006.01)
*A61L 31/00* (2006.01)
(Continued)

(52) U.S. Cl.
CPC .......... *A61F 2/0063* (2013.01); *A61L 31/005* (2013.01); *D04B 21/12* (2013.01);
(Continued)

(58) Field of Classification Search
CPC ............ A61F 2/0063; A61F 2002/0068; A61F 2210/0004; A61F 2/0045;
(Continued)

(56) References Cited

U.S. PATENT DOCUMENTS 2,259,025 A    10/1941    Cosgro
3,033,139 A    5/1962    Tateishi
(Continued)

FOREIGN PATENT DOCUMENTS

DE    10312674 A1    10/2003
DE    112007001732 T5    4/2011
(Continued)

OTHER PUBLICATIONS

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.
(Continued)

*Primary Examiner* — Katherine M Shi
(74) *Attorney, Agent, or Firm* — Shay Glenn LLP

(57) ABSTRACT

Materials for soft tissue repair, and in particular, material for hernia repair. These materials may be configured as an implant, such as a graft, that may be implanted into a patient in need thereof, such as a patient having a hernia or undergoing a hernia repair surgical procedure. These grafts may include a first layer comprising a substrate (e.g., mesh) and a second layer comprising a sheet of anti-adhesive material. The layers may be attached with a plurality of relatively small attachment sites that are separated by regions in which the two layers are not attached, to provide a highly compliant graft.

19 Claims, 26 Drawing Sheets

Related U.S. Application Data continuation of application No. 15/814,275, filed on Nov. 15, 2017, now Pat. No. 10,561,485, which is a continuation of application No. 15/498,409, filed on Apr. 26, 2017, now Pat. No. 9,820,843.

(60) Provisional application No. 62/327,494, filed on Apr. 26, 2016.

(51) Int. Cl.
  D04B 21/12     (2006.01)
  D04B 21/16     (2006.01)

(52) U.S. Cl.
  CPC .... D04B 21/165 (2013.01); *A61F 2002/0068* (2013.01); *A61F 2210/0004* (2013.01); *A61F 2210/0076* (2013.01); *A61F 2220/0075* (2013.01); *A61F 2250/0015* (2013.01); *A61F 2250/0031* (2013.01); *A61F 2250/0067* (2013.01); *A61L 2430/34* (2013.01)

(58) Field of Classification Search
  CPC ...... A61F 2210/0076; A61F 2210/0057; A61F 2002/009; A61F 2220/0075; A61F 2250/0015; A61F 2250/0031; A61F 2250/0067; A61L 31/005; A61L 2430/34; D04B 21/12; D04B 21/165; D10B 2509/08
  See application file for complete search history.

(56) References Cited

U.S. PATENT DOCUMENTS

| | | | |
|---|---|---|---|
| 3,054,406 A | 9/1962 | Usher | |
| 3,155,095 A | 3/1964 | Brown | |
| 3,364,200 A | 1/1968 | Ashton et al. | |
| 3,658,023 A | 4/1972 | Rossi | |
| 4,466,370 A | 8/1984 | Eguchi et al. | |
| 5,593,441 A | 1/1997 | Lichtenstein et al. | |
| 5,634,931 A | 6/1997 | Kugel | |
| 5,683,400 A | 11/1997 | McGuire | |
| 5,707,395 A | 1/1998 | Li | |
| 5,723,010 A | 3/1998 | Yui et al. | |
| 5,919,232 A | 7/1999 | Chaffringeon et al. | |
| 5,990,378 A | 11/1999 | Ellis | |
| 6,120,539 A | 9/2000 | Eldridge et al. | |
| 6,258,124 B1 | 7/2001 | Darois et al. | |
| 6,319,264 B1 | 11/2001 | Törmäla et al. | |
| 6,371,985 B1 | 4/2002 | Goldberg | |
| 6,383,201 B1 | 5/2002 | Dong | |
| 6,652,595 B1 | 11/2003 | Nicolo | |
| 6,814,748 B1 | 11/2004 | Baker et al. | |
| 6,962,120 B1 | 11/2005 | Fujikura et al. | |
| 7,824,420 B2 | 11/2010 | Eldridge et al. | |
| 7,946,236 B2 | 5/2011 | Butcher | |
| 8,074,591 B2 | 12/2011 | Butcher et al. | |
| 8,182,545 B2 | 5/2012 | Cherok et al. | |
| 8,236,342 B2 | 8/2012 | Thomas et al. | |
| 8,853,294 B2 | 10/2014 | Myung et al. | |
| 9,205,052 B2 | 12/2015 | Kim et al. | |
| 9,289,279 B2 | 3/2016 | Wilson et al. | |
| 9,295,757 B2 | 3/2016 | Patel et al. | |
| 9,326,840 B2 | 5/2016 | Mortarino | |
| 9,364,310 B2 | 6/2016 | Stopek | |
| 9,421,079 B2 | 8/2016 | Koullick et al. | |
| 9,468,705 B2 | 10/2016 | Geller | |
| 9,510,925 B2 | 12/2016 | Hotter et al. | |
| 9,554,887 B2 | 1/2017 | Lecuivre | |
| 9,585,838 B2 | 3/2017 | Hartounian et al. | |
| 9,770,414 B2 | 9/2017 | Garcia et al. | |
| 9,775,700 B2 | 10/2017 | Greenhalgh et al. | |
| 9,820,843 B2 | 11/2017 | Greenhalgh et al. | |
| 9,925,030 B2 | 3/2018 | Greenhalgh et al. | |
| 10,130,457 B2 | 11/2018 | Greenhalgh et al. | |
| 10,213,284 B2 | 2/2019 | Greenhalgh et al. | |
| 10,426,587 B2 | 10/2019 | Greenhalgh et al. | |
| 10,500,030 B2 | 12/2019 | Greenhalgh et al. | |
| 10,561,485 B2 | 2/2020 | Greenhalgh et al. | |
| 10,675,141 B2 | 6/2020 | Greenhalgh et al. | |
| 10,702,364 B2 | 7/2020 | Greenhalgh et al. | |
| 11,344,397 B2 | 5/2022 | Greenhalgh et al. | |
| 11,369,464 B2 | 6/2022 | Greenhalgh et al. | |
| 11,446,130 B2 | 9/2022 | Greenhalgh et al. | |
| 11,464,616 B2 | 10/2022 | Greenhalgh et al. | |
| 2001/0020188 A1 | 9/2001 | Sander | |
| 2002/0111392 A1 | 8/2002 | Cruise | |
| 2003/0023316 A1 | 1/2003 | Brown et al. | |
| 2003/0225355 A1 | 12/2003 | Butler | |
| 2004/0010320 A1 | 1/2004 | Huckle et al. | |
| 2004/0033212 A1 | 2/2004 | Thomson et al. | |
| 2004/0054376 A1 | 3/2004 | Ory et al. | |
| 2004/0078089 A1 | 4/2004 | Ellis et al. | |
| 2004/0138762 A1 | 7/2004 | Therin et al. | |
| 2004/0249457 A1 | 12/2004 | Smith et al. | |
| 2005/0070930 A1 | 3/2005 | Kammerer | |
| 2005/0113849 A1 | 5/2005 | Popadiuk et al. | |
| 2005/0113938 A1 | 5/2005 | Jamiolkowski et al. | |
| 2005/0118236 A1 | 6/2005 | Qiu et al. | |
| 2005/0255543 A1 | 11/2005 | Just et al. | |
| 2006/0178683 A1 | 8/2006 | Shimoji et al. | |
| 2006/0217747 A1 | 9/2006 | Ferree | |
| 2006/0229722 A1 | 10/2006 | Bianchi et al. | |
| 2007/0088434 A1 | 4/2007 | Frank | |
| 2007/0190108 A1 | 8/2007 | Datta et al. | |
| 2007/0224238 A1 | 9/2007 | Mansmann et al. | |
| 2008/0097601 A1 | 4/2008 | Codori-Hurff et al. | |
| 2008/0167729 A1 | 7/2008 | Nelson et al. | |
| 2008/0181928 A1 | 7/2008 | Hakimi-Mehr et al. | |
| 2009/0018655 A1 | 1/2009 | Brunelle et al. | |
| 2009/0054339 A1 | 2/2009 | Marshall et al. | |
| 2009/0069893 A1 | 3/2009 | Paukshto et al. | |
| 2009/0082864 A1 | 3/2009 | Chen et al. | |
| 2009/0216338 A1 | 8/2009 | Gingras et al. | |
| 2009/0306688 A1 | 12/2009 | Patel et al. | |
| 2009/0326577 A1 | 12/2009 | Johnson et al. | |
| 2010/0010114 A1 | 1/2010 | Myung et al. | |
| 2010/0028396 A1 | 2/2010 | Ward et al. | |
| 2010/0063599 A1 | 3/2010 | Brunelle et al. | |
| 2010/0100107 A1 | 4/2010 | Duggal et al. | |
| 2010/0120679 A1 | 5/2010 | Xu et al. | |
| 2010/0217388 A1 | 8/2010 | Cohen et al. | |
| 2010/0249929 A1 | 9/2010 | Kurz et al. | |
| 2010/0305500 A1 | 12/2010 | Lambert et al. | |
| 2010/0318108 A1 | 12/2010 | Datta et al. | |
| 2010/0318124 A1 | 12/2010 | Leung et al. | |
| 2011/0014153 A1 | 1/2011 | Derwin et al. | |
| 2011/0020420 A1* | 1/2011 | Bosley, Jr. | A61L 27/3633 623/23.72 |
| 2011/0125287 A1 | 5/2011 | Hotter et al. | |
| 2011/0196490 A1 | 8/2011 | Gadikota et al. | |
| 2011/0250264 A1 | 10/2011 | Schutt et al. | |
| 2011/0257761 A1 | 10/2011 | Mortarino | |
| 2011/0301717 A1 | 12/2011 | Becker | |
| 2012/0010637 A1 | 1/2012 | Stopek et al. | |
| 2012/0035608 A1 | 2/2012 | Marchitto et al. | |
| 2012/0082712 A1 | 4/2012 | Stopek et al. | |
| 2012/0095482 A1 | 4/2012 | Peterson et al. | |
| 2012/0143329 A1 | 6/2012 | Kim | |
| 2012/0165957 A1 | 6/2012 | Everland et al. | |
| 2012/0179176 A1 | 7/2012 | Wilson et al. | |
| 2012/0184974 A1 | 7/2012 | Becker | |
| 2012/0253464 A1 | 10/2012 | Hwang et al. | |
| 2013/0064772 A1 | 3/2013 | Swiss et al. | |
| 2013/0116799 A1 | 5/2013 | Derwin et al. | |
| 2013/0172994 A1 | 7/2013 | Becker | |
| 2013/0197300 A1 | 8/2013 | Koullick et al. | |
| 2013/0209547 A1 | 8/2013 | Garcia et al. | |
| 2013/0211307 A1 | 8/2013 | Evans et al. | |
| 2013/0267137 A1 | 10/2013 | Peniston et al. | |
| 2013/0303958 A1 | 11/2013 | Holm et al. | |
| 2013/0304098 A1 | 11/2013 | Mortarino | |
| 2013/0317286 A1 | 11/2013 | Bluecher et al. | |
| 2014/0090942 A1 | 4/2014 | Schlipper | |

(56) References Cited

U.S. PATENT DOCUMENTS

| | | |
|---|---|---|
| 2014/0094931 A1 | 4/2014 | Derwin et al. |
| 2014/0276993 A1 | 9/2014 | Reilly et al. |
| 2014/0364878 A1 | 12/2014 | Ladet et al. |
| 2015/0112434 A1 | 4/2015 | Felix et al. |
| 2015/0127103 A1 | 5/2015 | Seedhom |
| 2015/0267330 A1 | 9/2015 | Carrier et al. |
| 2015/0297798 A1 | 10/2015 | Badylak et al. |
| 2016/0058534 A1 | 3/2016 | Derwin et al. |
| 2016/0058589 A1 | 3/2016 | Bar et al. |
| 2016/0136289 A1 | 5/2016 | Puri et al. |
| 2016/0206580 A1 | 7/2016 | Los et al. |
| 2016/0262208 A1 | 9/2016 | Hsieh |
| 2016/0374791 A1 | 12/2016 | Lecuivre et al. |
| 2017/0027679 A1 | 2/2017 | Serban et al. |
| 2017/0086972 A1 | 3/2017 | Braido et al. |
| 2017/0245847 A1 | 8/2017 | Obermiller et al. |
| 2019/0008623 A1 | 1/2019 | Nemoto et al. |
| 2020/0297476 A1 | 9/2020 | Greenhalgh et al. |
| 2020/0330211 A1 | 10/2020 | Greenhalgh et al. |
| 2020/0360129 A1 | 11/2020 | Moses et al. |
| 2020/0397949 A1 | 12/2020 | Greenhalgh |
| 2021/0290416 A1 | 9/2021 | Hall et al. |
| 2022/0110749 A1 | 4/2022 | Hariton et al. |
| 2022/0273412 A1 | 9/2022 | Greenhalgh et al. |
| 2022/0296350 A1 | 9/2022 | Greenhalgh et al. |
| 2023/0293281 A1 | 9/2023 | Greenhalgh et al. |
| 2023/0338637 A1 | 10/2023 | Nazerali et al. |

FOREIGN PATENT DOCUMENTS

| | | |
|---|---|---|
| EP | 2198854 A2 | 6/2010 |
| EP | 2229918 A1 | 9/2010 |
| EP | 2300066 A2 | 3/2011 |
| EP | 2344133 A2 | 7/2011 |
| RU | 2524196 C2 | 7/2014 |
| WO | WO00/57812 A1 | 10/2000 |
| WO | WO02/078568 A1 | 10/2002 |
| WO | WO03/082363 A1 | 10/2003 |
| WO | WO03/094781 A1 | 11/2003 |
| WO | WO2008/095038 A1 | 8/2008 |
| WO | WO2012/017415 A2 | 2/2012 |
| WO | WO2017/050837 A1 | 3/2017 |
| WO | WO2017/191276 A1 | 11/2017 |
| WO | WO2017/223462 A1 | 12/2017 |

OTHER PUBLICATIONS

Franklin et al.; Uptake of tetracycline by aortic aneurysm wall and its effect on inflammation and proteolysis; British Journal of Surgery; 86(6); pp. 771-775; Jun. 1999.

Mayo Clinic; Placement of Breast Implants; retrieved May 25, 2017 from http://www.mayoclinic.org/placement-of-breast-implants/img-20007384; 1 pg; May 25, 2017.

Pyo et al.; Targeted gene disruption of matrix metalloproteinase-9 (gelatinase B) suppresses development of experimental abdominal aortic aneurysms; The journal of Clinical Investigation; 105(11); pp. 1641-1649; Jun. 2000.

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdominal aortic; Circulation; 100; pp. 48-54, 8 pages; Jul. 1999.

Xu et al.; Sp1 increases expression of cyclooxygenase-2 in hypoxic vascular endothelium implications for the mechanisms of aortic aneurysm and heart failure; journal of Biological Chemistry; 275(32); pp. 24583-24589; Aug. 2000.

Greenhalgh et al.; U.S. Appl. No. 17/932,856 entitled "Textured medical textiles," filed Sep. 16, 2022.

Greenhalgh ; U.S. Appl. No. 18/157,653 entitled "Surgical repair graft," filed Jan. 20, 2023.

Nazerali; U.S. Appl. No. 17/447,166 entitled "Subcutaneous and pocket irrigator," filed Sep. 8, 2021.

Romano et al.; U.S. Appl. No. 18/353,858 entitled "Nonuniform embroidered soft tissue implant structure," filed Jul. 17, 2023.

Greenhalgh et al.; U.S. Appl. No. 18/511,680 entitled "Corner-lock stitch patterns," filed Nov. 16, 2023.

* cited by examiner

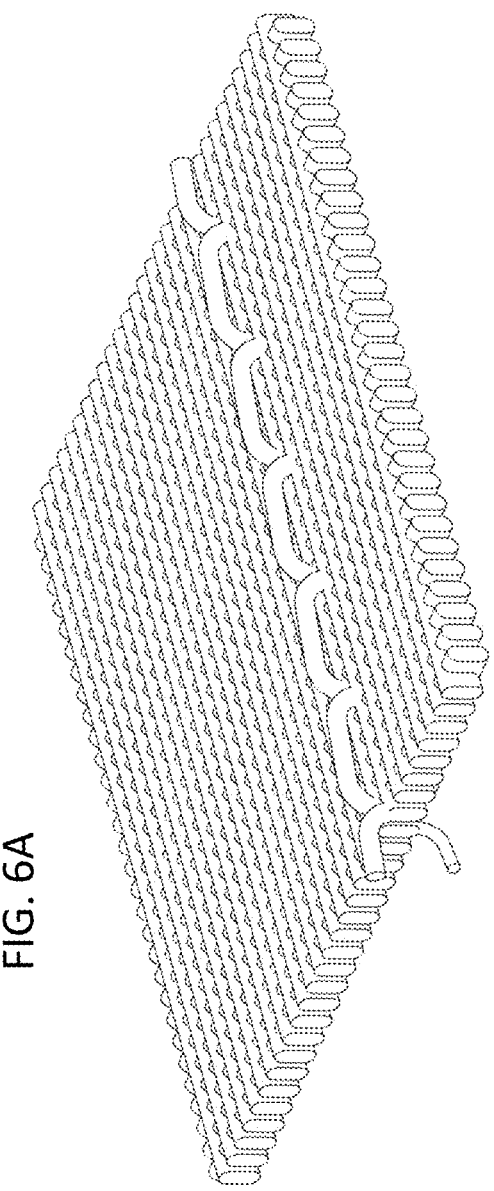
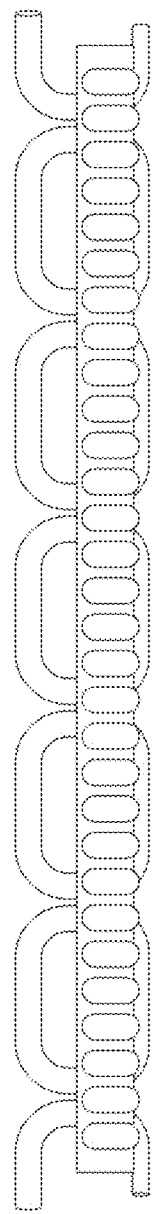
FIG. 6A
FIG. 6B

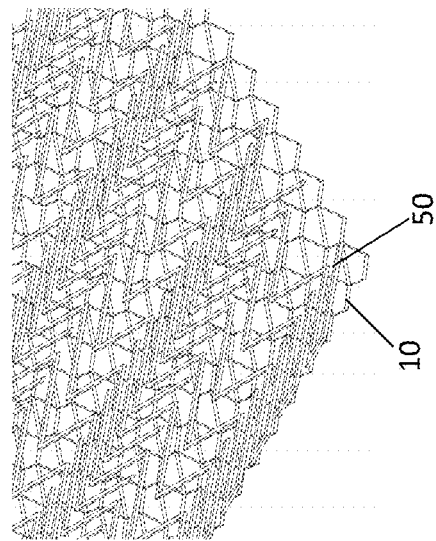
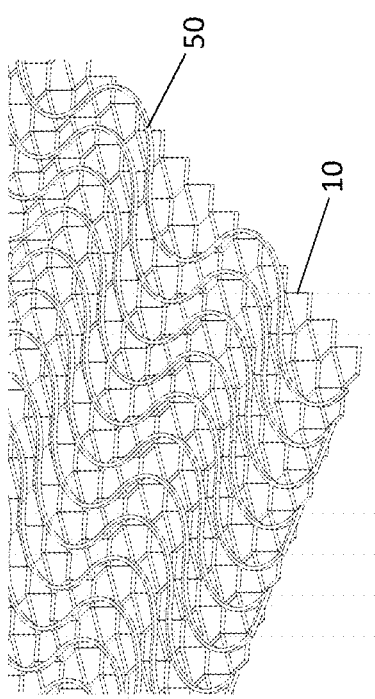
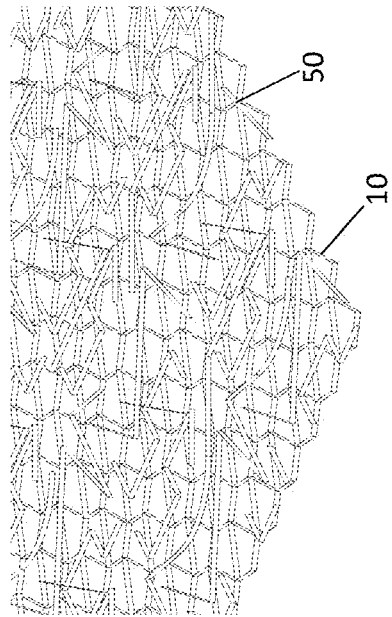

HERNIA REPAIR GRAFTS HAVING ANTI-ADHESION BARRIERS

CROSS REFERENCE TO RELATED APPLICATIONS

This patent application is a continuation of U.S. patent application Ser. No. 16/792,068, filed Feb. 14, 2020, titled "HERNIA REPAIR GRAFTS HAVING ANTI-ADHESION BARRIERS," now U.S. Pat. No. 11,464,616, which is a continuation of U.S. patent application Ser. No. 15/814,275, filed Nov. 15, 2017, titled "HERNIA REPAIR GRAFTS HAVING ANTI-ADHESION BARRIERS," now U.S. Pat. No. 10,561,485, which is a continuation of U.S. patent application Ser. No. 15/498,409, filed Apr. 26, 2017, titled "HERNIA REPAIR GRAFTS HAVING ANTI-ADHESION BARRIERS," now U.S. Pat. No. 9,820,843, which claims priority to U.S. Provisional Patent Application No. 62/327,494, filed on Apr. 26, 2016, titled "ADHESION BARRIERS SEWN ON TO OR SEWN INTO IMPLANTABLE SOFT TISSUE REPAIR SUBSTRATES," each of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses (e.g., devices and systems, including grafts) and methods described herein relate generally to the field of soft tissue repair. More particularly, described herein are graft materials for soft tissue repair that include an adhesion barrier that inhibits the formation of post-surgical adhesions while advantageously matching the biomechanical properties of the tissue during healing and recovery.

BACKGROUND

Adhesions are fibrous bands of connective tissue that form between tissues and organs in the body that are not normally connected together, or that form in a way that is different from the normal connective tissue anatomy between tissues and organs in the body. Adhesions commonly form after surgery on the abdomen or the pelvic regions, though post-surgical adhesions may form anywhere in the body. In certain cases, adhesions may cause complications such as pain or obstruction of the organs to which they connect.

Adhesions generally begin forming shortly after surgery, and continue to develop thereafter. There are no known treatments to reverse adhesion formation. If adhesions lead to complications in the patient, the typical treatment is to remove them surgically. The best approach to adhesion management is prevention.

Various products are on the market for prevention of adhesion formation. These products are not 100% effective, though their use fairly consistently substantially reduces adhesion formation. These products take on many forms, such as gels and pastes that are applied to surgical sites within the body, and are gradually resorbed over a the course of a few days.

Another anti-adhesion product is a physical barrier, such as polytetrafluoroethylene membranes. The barriers need not be permanent implants and, to this end, oxidized regenerated cellulose (ORC) sheets are commonly implanted within surgical sites. These ORC sheets are resorbed over the course of a few days, and are typically well-tolerated by patients.

Adhesions may be particularly troublesome when repairing soft tissue, such as a hernia, in which success and recovery of the procedure in both the short and long term may be determined in part by the biomechanical response of the graft used to repair the tissue. The compliance of the graft used to repair the tissue may largely affect outcome of the procedure; it is generally better to match the compliance of the tissue, and avoid both over-compliant and under-compliant implants. However the compliance of the implant may change over time, in part because of the tissue response, including the presence of adhesions. Adhesions may change the compliance of the implant.

Hernia repair surgery, which is a form of abdominal or pelvic surgery, often induces adhesion formation. Certain hernia repair procedures involve the implantation of synthetic or biologic mesh materials that support biologic loads at the site of herniation while the body repairs itself. But over time, these implanted hernia repair substrates may become progressively infiltrated with and covered with scar tissue, and themselves become a source of adhesions.

There remains a need for adhesion prevention and control, particularly with respect to hernia repair surgery. Further, there is generally a need for hernia repair grafts that are sufficiently compliant and that maintain their biomechanical properties, including compliance, over time while implanted into a patient.

SUMMARY OF THE DISCLOSURE

The present invention relates to materials for soft tissue repair, and in particular, material for hernia repair. These materials may be configured as an implant, such as a graft, that may be implanted into a patient in need thereof, such as a patient having a hernia or undergoing a hernia repair surgical procedure. Advantageously, these materials (and any apparatuses such as devices and systems, including grafts) are particularly well suited for surgical implantation over time in repair of a body wall cavity, and may have biomechanical properties, and particularly a compliance, that matches that of a patient's body both initially (e.g., immediately upon implantation) and over time following implantation. Further, these materials (and any apparatuses such as devices and systems, including grafts) may prevent tissue attachments.

The apparatuses (e.g., grafts, implants, etc.) may comprise a substrate material that may be a mesh. The substrate (mesh) may be a biotextile, medical textile, or both a biotextile and medical textile. These apparatuses may also include an adhesion barrier that is attached at discrete locations (e.g., sewn or embroidered into the substrate mesh or sewn onto the substrate mesh) while still allowing sliding between the substrate mesh and the anti-adhesion layer (adhesive barrier) at regions adjacent and/or between the discrete adhesion locations. The substrate mesh may comprise an extracellular matrix, or a scaffold, or a hernia repair scaffold, patch, or mesh; the substrate is typically arranged in an open-cell mesh, and may be referred to herein as a "mesh". The substrate may comprise a biocompatible film.

The substrate (e.g., mesh, or mesh plus embroidered pattern on the mesh, etc.) may be referred to collectively as a first layer.

Any of the substrates described herein may be a mesh formed of a first material that is non-bioabsorbable (e.g., a non-bioabsorbable mesh). These materials may also include a first pattern of a filament (e.g., thread, wire, braid, monofilament, multi-filament, etc.) that is sewn or embroidered into the mesh. This first pattern may be embroidered with a bioabsorbable material or, if the mesh is bioabsorbable, a material having a second bioabsorbable profile; e.g., that is absorbed more quickly than the mesh material. The first pattern may be a grid or array of lines of stitches that are parallel; in some variation the first pattern may comprise a plurality of sub-patterns that are arranged offset from each other and overlapping. The material forming the first pattern, and the overall first pattern, may have a lower compliance than the mesh. Thus, the final compliance of the substrate may be the compliance of the mesh and the first pattern embroidered onto the mesh.

The compliance (e.g., flexibility) of a material may refer to the mechanical property of the material undergoing elastic deformation when subjected to an applied force. It is the reciprocal of stiffness. Compliance may be described as a percent compliance strain. Materials that deform easily are said to be compliant.

In any of the apparatuses (materials, grafts, etc.) described herein, the adhesion barrier may comprise one or more layers of an adhesion barrier material. The substrate may comprise one or more, or a plurality of layers of the biotextile and/or medical textile. The material may preferably be an extracellular material (ECM), such as extracellular matrix derived from one or more of the dermis, pericardium, peritoneum, intestine, stomach, or forestomach. The adhesion barrier may be referred to collectively as a second layer.

The second (anti-adhesion layer or adhesion barrier layer) layer may be attached to the first (substrate, e.g., mesh or mesh and embroidered pattern) layer in a manner that does not substantially change the compliance. In practice, this may mean that the compliance of the first and second layers separately or when loosely stacked on top of each other, is not changed more than a few percent when attached together as described herein. For example, the compliance of the material when the first (mesh or mesh and first embroidered pattern) and second (e.g., anti-adhesion layer) are attached together by a pattern, e.g., a second pattern or "attachment pattern", of discrete attachment sites may be within 20% or less (e.g., within 19%, 18%, 17%, 16%, 15%, 14%, 13%, 12%, 11%, 10%, 9%, 8%, 7%, 6%, 5%, or less, such as within 10% or less, or within 15% or less, etc.) of the compliance of either the first layer alone or the second layer alone, or a loose stack of the first and second layer (e.g., the two stacked onto each other as layers that are not attached).

The discrete attachment sites may be stitches connecting the first layer to the second layer, or they may be chemical or material adhesives between the two layers in small, discrete locations, such as an adhesive or glue material that is biocompatible and adheres the first (e.g., mesh, mesh that is embroidered, etc.) layer to the second (e.g., ECM) layer. The adhesive may be any appropriate biologically compatible adhesive. The discrete attachment sites may refer to relatively small diameter regions which may be regularly shaped or irregularly shaped. When the discrete attachments are stitches sewn between the two, the discrete attachment sites may have a diameter of the stitching material (e.g., fiber, thread, yarn, etc.). For example, the discrete attachment sites may have a diameter of between about 0.001 inch and 0.20 inches (e.g., between about 0.001 inches to about 0.010 inches, between about 0.001 to about 0.060 inches, etc.).

When the adhesion barrier is sewn or embroidered to the substrate, the sewing or embroidery may comprise a stitch pattern (e.g., an attachment pattern) comprising at least one filament, thread, or yarn comprising an adhesion barrier material. Note that these stitch patterns may be patterns of discrete attachment sites arranged in the pattern; the adhesion site may refer to connection or stitch between the two layers. Thus any of these stitch patterns may refer to the pattern of discrete attachment sites between the two layers (e.g., the substrate/mesh layer and the anti-adhesion layer/ECM). The stitch pattern may comprise a plurality of straight lines oriented along one or more axes of the substrate. A subset of straight lines oriented along different axes of the substrate may intersect, and may form a grid pattern. The stitch pattern may comprise a plurality of parallel lines. The stitch pattern may comprise a plurality of lines arranged in a zig-zag. A subset of the lines in a zig-zag may comprise a different amplitude, frequency, or amplitude and frequency relative to another subset of the lines in a zig-zag in the stitch pattern. The stitch pattern may comprise a plurality of lines arranged in a pattern comprising a plurality of curves, including a wave pattern (e.g., a sinusoidal wave) or an oscillating line pattern. A subset of the lines in a curve pattern may comprise a different amplitude, frequency, or amplitude and frequency relative to another subset of the lines in a curve in the stitch pattern. The stitch pattern may be continuous or comprise breaks or interruptions. The stitch pattern may comprise a corner-lock stitch pattern. The stitch pattern may comprise an upper filament, thread, or yarn and a lower filament, thread, or yarn. The upper filament, thread, or yarn may comprise a larger diameter relative to the a lower filament, thread, or yarn, or may comprise substantially the same diameter relative to the lower filament, thread, or yarn, or may comprise a smaller diameter relative to the lower filament, thread, or yarn. The upper filament, thread, or yarn and the lower filament, thread, or yarn may comprise any one or more of chitosan, hyaluronic acid, icodextrin, fibrin, poly(L-lactide-co-D,L-lactide)/polylactic acid, polytetrafluoroethylene, or oxidized regenerated cellulose, including any combination thereof.

In general, the attachment between the first layer (substrate layer, e.g., mesh) and the second (anti-adhesive) layer may be configured to flexibly attach the two layers, so that the attachment of the two layers does not change the compliance more than a nominal (e.g., 15% or less) amount. This flexible attachment may be achieved (at least in part) by including regions between the discrete attachment sites that are not attached, so that the first layer and second layer may move (e.g., slide) relative to each other as the material is bent or pulled. For example, the discrete attachment sites may be separated by a distance of greater than 0.02 inches (e.g., 0.5 mm) (e.g., greater than 0.01 inches, 0.02 inches, 0.03 inches, 0.04 inches, 0.05 inches, 0.06 inches, 0.07 inches, 0.08 inches, 0.09 inches, 0.1 inches, 0.2 inches, 0.3 inches, 0.4 inches, 0.5 inches, etc.). The discrete attachment sites may be separated by a distance of between 0.02 inches and 1.2 inches (e.g., between 0.5 mm and 30 mm) (e.g., between 0.01 inches and 1.5 inches, between 0.01 inches and 1.2 inches, between 0.01 inches and 1.1 inches, between 0.02 inches and 1 inch, between 0.02 inches and 0.9 inches, between 0.02 inches and 0.8 inches, etc.). The density of the discrete attachment sites may be uniform or non-uniform. As mentioned above, the discrete attachment sites may be distributed in a pattern such as a grid (or overlapping grids). The density (e.g., average density) of attachment sites may be relatively low. For example, the density of attachment sites may be less than about 10 attachments/mm$^2$ (e.g., less than about 15 attachments/mm$^2$, less than 10 attachments/mm$^2$, less than 9 attachments/mm$^2$, less than 8 attachments/mm$^2$, less than 7 attachments/mm$^2$, less than 6 attachments/mm$^2$, less than 5 attachments/mm$^2$, etc.).

When the second layer (e.g., the adhesion barrier/anti-adhesive material) is sewn or embroidered onto the substrate (e.g., mesh, or mesh plus first embroidered pattern), the second layer may comprises one or more sheets of adhesion barrier material, such as ECM. As mentioned, after attachment with the stitching pattern described herein, the one or more sheets may be movable relative to the substrate. For example, the one or more sheets may be joined to the substrate with a stitch pattern comprising at least one filament, thread, or yarn. The stitching material (e.g., filament, thread, etc.) may be formed of any appropriate material, including a polymeric material. The stitching material may be formed of the same material as the adhesion barrier sheets.

The attachment stitch pattern securing the substrate mesh to the anti-adhesive material may comprise a plurality of stitch islands, whereby the at least one filament, yarn, or thread are sewn at discreet locations about the substrate, with regions that are unattached (e.g., having no stitch pattern, filament, yarn, or thread) in between stitch islands. The stitched attachment pattern may comprise a plurality of straight lines oriented along one or more axes of the substrate. A subset of straight lines oriented along different axes of the substrate may intersect, and may form a grid pattern. The stitched attachment pattern may comprise a plurality of parallel lines. The stitch pattern may comprise a plurality of lines arranged in a zig-zag. A subset of the lines in a zig-zag may comprise a different amplitude, frequency, or amplitude and frequency relative to another subset of the lines in a zig-zag in the stitch pattern. The stitched attachment pattern may comprise a plurality of lines arranged in a pattern comprising a plurality of curves, including a wave pattern (e.g., a sinusoidal wave) or an oscillating line pattern. A subset of the lines in a curve pattern may comprise a different amplitude, frequency, or amplitude and frequency relative to another subset of the lines in a curve in the stitch pattern. The stitched attachment pattern may be random. The stitched attachment pattern may be continuous or comprise breaks or interruptions. The stitched attachment pattern may comprise a corner-lock stitch pattern. The stitched attachment pattern may comprise an upper filament, thread, or yarn and a lower filament, thread, or yarn. The upper filament, thread, or yarn may comprise a larger diameter relative to the lower filament, thread, or yarn, or may comprise substantially the same diameter relative to the lower filament, thread, or yarn, or may comprise a smaller diameter relative to the lower filament, thread, or yarn. The upper filament, thread, or yarn and the lower filament, thread, or yarn may comprise any one or more of chitosan, hyaluronic acid, icodextrin, fibrin, poly(L-lactide-co-D,L-lactide)/polylactic acid, polytetrafluoroethylene, or oxidized regenerated cellulose, including any combination thereof. The one or more adhesion barrier sheets may comprise any one or more of chitosan, hyaluronic acid, icodextrin, fibrin, poly(L-lactide-co-D,L-lactide)/polylactic acid, polytetrafluoroethylene, or oxidized regenerated cellulose, including any combination thereof.

Methods for making any of the implants (e.g., grafts) or substrate materials are also described herein. Methods may comprise, for example, sewing or embroidering an adhesion barrier material into one or more stitched attachment patterns to secure the anti-adhesive material (sheet, e.g., ECM) to any of the substrate materials (e.g., meshes) described or exemplified herein. In some aspects, such methods comprise, for example, sewing one or more sheets comprising an adhesion barrier material onto any substrate material described or exemplified herein. The substrate may first have a first pattern of embroidered onto it (e.g., compliance limiting pattern) in a material having a greater bioabsorbability than the substrate material. For example the mesh may be relatively highly compliant but may have a compliance-limiting stitching pattern embroidered onto it with a lower compliance material; this mesh with an embroidered material may then be stitched in a second (attachment) pattern of discrete attachment sites (e.g., stitches).

Any of the apparatuses (e.g., grafts) described herein may be used to repair tissue. For example, described herein are methods for inhibiting adhesions while repairing or reconstructing tissue in a subject in need thereof. Such methods may generally comprise implanting an implant or substrate material comprising an adhesion barrier sewn or embroidered into the implant or substrate or comprising one or more adhesion barrier layers sewn onto the implant or substrate at a location in the body of the subject in need of tissue repair or tissue reconstruction. The tissue may be any tissue in the body, including soft tissue. The tissue may comprise a hernia, such that the implant or substrate is used to repair the herniation. Once implanted, the adhesion barrier inhibits adhesions between tissue in the body and the implant or substrate, and may also further inhibit adhesions between adjacent tissues in the body that is proximal to the implant. The subject may be human being or other animal (e.g., veterinary animal, non-human animal, etc.).

For example, described herein are hernia repair grafts. A hernia repair graft may include: a first layer comprising a mesh; a second layer comprising a sheet of anti-adhesive material, wherein the second layer is flexibly attached to the first layer with a pattern of discrete attachment sites, wherein the pattern of discrete attachment sites alters the compliance of the stacked first and second layers by less than 15% and adjacent regions of the first layer and second layer between the discrete attachment sites may slide relative to each other.

A hernia repair graft may include: a first layer comprising a knitted, non-bioabsorbable mesh and a first pattern embroidered into the mesh with a bioabsorbable material; a second layer comprising a sheet of anti-adhesive material attached at discrete attachment sites along the first layer such that adjacent discrete attachment sites are separated by a distance of between 0.5 mm and 30 mm, and adjacent regions of the first layer and the second layer between the discrete attachment sites may slide relative to each other.

Any of the hernia repair grafts described herein may include: a first layer stacked onto a second layer; wherein the first layer comprises: a mesh formed of a non-absorbable material and a first pattern stitched into the mesh with a bioabsorbable material; wherein the second layer comprises an anti-adhesive material comprising a plurality of sheets of extracellular matrix material (ECM); further wherein the second layer is flexibly attached to the first layer with a second pattern of discrete stitched attachment sites, wherein the second pattern of discrete stitched attachment sites is less dense than the first pattern stitched into the mesh, wherein adjacent discrete attachment sites are separated by a distance of between 0.5 mm and 30 mm and wherein adjacent regions of the first layer and second layer between the discrete attachment sites may slide relative to each other.

In any of the grafts described herein, the second pattern (e.g., the attachment pattern) may be a second stitching pattern of discrete attachment sites. The second pattern may be less dense than the first pattern in the plane of the first layer.

In general the substrate may be a mesh. The mesh may be a knitted mesh, a woven mesh, or a formed mesh. The mesh may be formed of polypropylene, polytetrafluoroethylene (PTFE), nylon, polyester, or the like (including combinations of these). The mesh may have an open cell pore diameter of between 0.5 mm and 6 mm (e.g., 0.0197 inches and 0.24 inches). The mesh may be formed of a warp knitted filament having a diameter of between 0.001 inch and 0.010 inches. For example, the mesh may be formed of a warp knitted filament having a diameter of between 0.003 inch and 0.006 inches. The mesh may be formed of a plurality of fibers that are knitted together (multi-filament) or a mono-filament. In some variations multi-filament fibers (for either or both the mesh and the sewn materials) may be preferred because they may be stronger.

As mentioned above, the first pattern (e.g., the pattern embroidered into the mesh) may comprise adjacent lines of stitching that cross to interlock at regular intervals. The first pattern may comprise a first stitching sub-pattern and a second stitching sub-pattern, wherein the first stitching sub-pattern overlaps with the second stitching sub-pattern and the first stitching sub-pattern is rotated between 25 and 65 degrees relative to the second stitching sub-pattern.

The anti-adhesive material may comprise extracellular matrix (ECM), such as ECM derived from one or more of the dermis, pericardium, peritoneum, intestine, stomach, or forestomach. The second layer may comprise a plurality of stacked sheets of the extracellular matrix (ECM) material.

As mentioned, the discrete attachment sites may comprise a second stitching pattern, such as a grid pattern. The adjacent discrete attachment sites may be separated by a minimum distance or a range of distanced (e.g., between 0.5 mm and 30 mm). The second layer may be flexibly attached to the first layer with a second pattern of discrete attachment sites having a density of attachment sites that is less than, e.g., about 10 attachments/mm$^2$.

In general, in any of these materials (e.g., hernia repair grafts) the compliance strain of the material may be between 10-30% at 16 N/cm. This range of compliance may be particularly well suited to match the compliance of the tissue that the hernia is repairing, to prevent discomfort and potential re-injury of the repair site. Within this range, at least when initially implanted, the material may result in far superior medical outcomes; outside of this range the implant may be less comfortable and may require further future treatment. It has also be found to be advantageous to have the compliance of the hernia repair graft increase over time, as the surrounding tissues heals and grows (e.g., into the implant). As mentioned above, the embroidered first pattern may decreases the compliance of the mesh so that the compliance of the hernia repair apparatus will increase over time in a patient as the bioabsorbable material is absorbed. The attachment sites attaching the second layer to the first layer may form a grid pattern of cells each having a diameter, e.g., of between 10 mm and 35 mm.

A hernia repair graft may include: a first layer stacked onto a second layer; wherein the first layer comprises: a mesh formed of a non-absorbable material and a first pattern embroidered into the mesh with a bioabsorbable material; wherein the second layer comprises a sheet of anti-adhesive material comprising an extracellular matrix (ECM) material; further wherein the second layer is flexibly attached to the first layer with a second pattern of discrete attachment sites, wherein the second pattern of discrete attachment sites alters the compliance of the stacked first and second layers by less than 15% and adjacent regions of the first layer and second layer between the discrete attachment sites may slide relative to each other.

A hernia repair graft may include: a first layer stacked onto a second layer; wherein the first layer comprises: a mesh formed of a non-absorbable material and a first pattern stitched into the mesh with a bioabsorbable material; wherein the second layer comprises an anti-adhesive material comprising a plurality of sheets of extracellular matrix material (ECM); further wherein the second layer is flexibly attached to the first layer with a second pattern of discrete stitched attachment sites, wherein the second pattern of discrete stitched attachment sites is less dense than the first pattern stitched into the mesh, and wherein adjacent regions of the first layer and second layer between the discrete attachment sites may slide relative to each other.

A hernia repair graft may include: a first layer stacked onto a second layer; wherein the first layer comprises: a mesh formed of a non-absorbable material and a first pattern stitched into the mesh with a bioabsorbable material, wherein the first pattern decreases the compliance of the mesh so that the compliance of the hernia repair apparatus will increase over time in a patient as the bioabsorbable material is absorbed; wherein the second layer comprises an anti-adhesive material comprising a sheet of extracellular matrix material (ECM); further wherein the second layer is flexibly attached to the first layer with a second pattern of discrete stitched attachment sites, wherein adjacent discrete attachment sites are separated by a distance of between 0.5 mm and 30 mm and wherein the second pattern of discrete stitched attachment sites is less dense than the first pattern stitched into the mesh, and further wherein adjacent regions of the first layer and second layer between the discrete attachment sites may slide relative to each other.

As mentioned above, also described herein are methods for repairing a hernia in a subject. These methods may include implanting any of the hernia repair grafts described herein into the body of the subject at a location within the body in need of hernia repair or reconstruction, thereby repairing or reconstructing the hernia and inhibiting the formation of adhesions between the body and the implant.

Also described herein are methods of making a hernia repair graft. For example a method of making a hernia repair graft may include: embroidering a first pattern into a non-absorbable mesh using a bioabsorbable material, wherein the first pattern decreases the compliance of the mesh; attaching a sheet of an anti-adhesive material comprising a sheet of extracellular matrix material (ECM) to the mesh at a plurality of discrete attachment sites, wherein the discrete attachment sites are separated by a distance of between 0.5 mm and 30 mm and wherein the second pattern of discrete stitched attachment sites is less dense than the first pattern stitched into the mesh, and further wherein adjacent regions of the mesh and sheet of anti-adhesive material between the discrete attachment sites may slide relative to each other.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings. The various features of the drawing are not to scale. On the contrary, the dimensions of the various features are arbitrarily expanded or reduced for clarity.

FIG. 2A shows an island stitch pattern, with the stitches forming small islands. FIG. 2B shows an island stitch pattern, with the stitches forming larger islands. FIG. 2C shows a grid stitch pattern. FIG. 2D shows a zig-zag stitch pattern. FIG. 2E shows a curve stitch pattern. FIG. 2F shows an interrupted stitch pattern. FIG. 2G shows a random stitch pattern.

In FIG. 3, the embroidering threads may be made of any appropriate material, including an adhesion barrier material, and are sewn (embroidered) into the mesh substrate. In the first two panels, the mesh substrate is on the bottom with the stitch pattern (threads sewn as a zig-zag pattern in this example) above them in the exploded view. In the third panel, the stitch pattern is shown sewn into the mesh substrate.

FIG. 6A shows a representation of a substrate fabric or mesh into which threads (e.g., of an adhesion barrier material) have been sewn. The upper thread has a larger diameter relative to the lower thread. FIG. 6B shows a side view of the threads sewn into the substrate.

FIGS. 8A through 8G show different stitch patterns that may be used to embroider a mesh substrate. FIG. 8A shows an example of a grid pattern of threads sewn into the mesh substrate. FIG. 8B shows an example of a zig-zag pattern of threads sewn into the mesh substrate. FIG. 8C shows an example of a higher density (relative to the pattern shown in FIG. 8B) zig-zag pattern of threads sewn into the mesh substrate, with the threads having a larger diameter (relative to the pattern shown in FIG. 8B). FIG. 8D shows an example of a zig-zag pattern of barrier threads sewn into the mesh substrate, with the zig-zag pattern having different amplitude and frequency (relative to the pattern shown in FIG. 8B). FIG. 8E shows an example of a curved pattern of threads sewn into the mesh substrate. FIG. 8F shows an example of an interrupted pattern of threads sewn into the mesh substrate. FIG. 8G shows an example of a random pattern of threads sewn into the mesh substrate.

DETAILED DESCRIPTION

Figure 1:
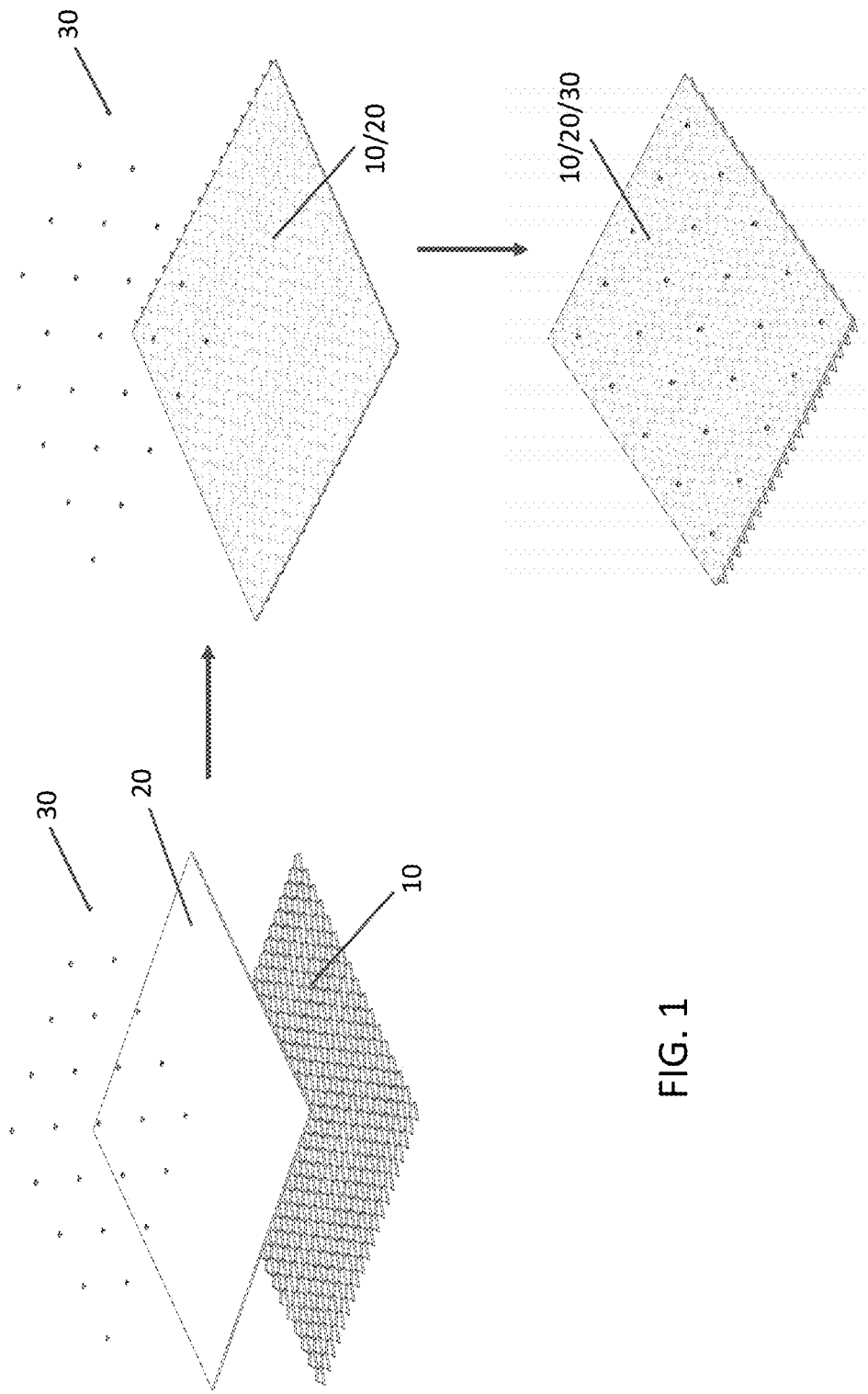
FIG. 1 shows an example of an adhesion barrier (e.g., ECM) to a mesh substrate using a grid of island-based embroidery stiches. In the first panel, the barrier (center), mesh substrate (bottom), and island stitches (top) are shown in an exploded view. In the second panel, the barrier has been placed atop of the mesh substrate, with the island stitches not yet applied. In the third panel, the stitch pattern has been embroidered into the barrier and mesh substrate layers, joining them into a substrate-barrier unit.

Described herein are apparatuses (e.g., devices, systems, materials, including but not limited to grafts, such as hernia repair grafts), methods for repairing soft tissue using such apparatuses and methods of making these apparatuses. These apparatuses may have desirable biomechanical and biochemical properties, including having a compliance that matches the body, and that changes over time in the body as portions are controllably absorbed in a manner that promotes healing and strengthen of the resulting tissue. Further, these apparatuses may include an anti-adhesion (e.g., "adhesion barrier") barrier on one or both sides of the relatively flat material (e.g., graft).

In general, these apparatuses may include a first layer and a second layer that are flexibly attached through a plurality small and discrete attachment sites distributed between the layers. The first layer, or substrate, may include a mesh. The mesh may be reinforced with one or more filaments embroidered in a first pattern. The mesh may have a first compliance and the compliance of the mesh may be decreased when reinforced with the embroidered pattern. The second layer generally includes an anti-adhesion layer, which may comprise one or more sheets of material, such as a biologic (e.g., ECM) the like.

As described in greater detail below, an apparatus may include a first layer comprising a mesh and a second layer comprising a sheet of anti-adhesive material. Examples of the first layer are provided herein, including examples having an embroidered pattern. The second layer may include one or more sheets of anti-adhesive material stacked atop each other. The first layer may be attached to the second layer with a plurality of relatively small attachment sites that are separated by regions in which the two layers are not attached. The sizes of the discrete attachment sites, the spacing between discrete attachment sites, and/or the density (e.g., average density) and/or pattern(s) of attachment sites may be controlled so that attachment of the two layers does not change the relative compliance of the first and/or second layer. Specifically, the attachment sites may change the overall compliance of the material (e.g., graft) 15% or less (e.g., 13% or less, 10% or less, 9% or less, 8% or less, 7% or less, 6% or less, 5% or less, etc.) compared to the compliance of either the first layer, the second layer, or a stack of the first and second layer that are not connected together. The flexible attachment between these two layers may refer to the ability of the regions of the first and second layer between the discrete attachment sites to slide relative to each other.

The discrete attachment sites may be stitches and/or chemical adhesives (e.g., glues). The discrete attachment sites may be separated from one another (or from adjacent groups of one another) by a distance of between 0.5 mm and 30 mm. The discrete attachment sites may have a diameter of between about 0.001 inch and 0.20 inches (e.g., between about 0.001 inches to about 0.010 inches, between about 0.001 to about 0.060 inches, etc.). The discrete attachment sites may be individual attachment sites (e.g., threads passing through the layers) or small groups of attachment sites (e.g., a plurality of threads that intersect and/or interlock as they pass through the material).

Adhesion barriers may be sewn onto or sewn into surgical implants such as a biotextile or medical textile (e.g., a hernia repair scaffold). The combination of the substrate or scaffold (e.g., mesh) and the adhesion barrier (e.g., sheet or sheets of ECM) may inhibit adhesions between the implanted scaffold and other tissues in the body. The adhesion barrier further imparts additional benefits into the scaffold, including strength and axial stiffness, as well as benefits to the implantation procedure such as placement orientation and additional suturing points. In addition to adhesion inhibition, the scaffold-adhesion barrier combination provides additional benefits to the patient as it lessens the need to implant a secondary adhesion barrier or to apply an anti-adhesion material at the surgical site, thereby lessening the potential for an infection or other complication.

Biotextile or medical textile scaffolds such as meshes may be used for soft tissue repair or reconstruction and, in this capacity, may generally be surgically implanted within the body. Such scaffolds may serve, for example, to replace or reinforce diseased or damaged soft tissue, or to hold internal organs in place in the case of a hernia repair. In some cases, these scaffolds are intended to be a permanent fixture within the body. In other cases, these scaffolds are intended to be a temporary fixture within the body such that they are made of a material that is gradually resorbed by the body as it is replaced by the body's own tissue.

The substrate material may be any material onto or into which an adhesion barrier may be sewn according to this disclosure ("substrate," "scaffold," and "substrate material" and "substrate materials" are used interchangeably herein). A substrate material may be a natural or synthetic material, may be a textile, and may be knitted, braided, woven or non-woven. Typical substrate materials may preferably include, but are not limited to, meshes. The substrate material may have any thickness, or length and width dimensions. The substrate material may be a biotextile or a medical textile. Biotextiles or medical textiles may be implantable in or on the human body. Thus, a substrate or substrate material may be an implant or a part of an implant.

Although the substrate may preferably be non-absorbable (e.g., having a very low bioabsorbability). Biotextiles include biocompatible materials, which may also include bioabsorbable materials. Biotextiles may be synthetic or may be obtained or derived from living tissue. Living tissue includes, for example dermis/skin tissue (and sub-tissue, extracellular matrices), pericardium, peritoneum, amnion, intestine, stomach, forestomach, and other suitable tissues. The animal source may be any suitable animal, including a mammal such as human, pig, cow, or sheep, or may be synthesized, for example, by recombinant expression. Biotextiles may be biodegradable or resorbable. Biotextiles may comprise collagen, or reconstituted collagen. Some non-limiting examples of biotextiles include extracellular matrix-derived tissue scaffolds or patches, autograft tissue, allograft tissue, and xenograft tissue, as well as artificial skin, artificial heart valves, and other implantable prosthetics. Medical textiles include biocompatible materials, which may include synthetic materials. Some non-limiting examples of medical textiles include hernia repair patches or meshes.

As mentioned both the scaffold and the anti-adhesive layers may be medical textiles and/or may comprise a biodegradable or resorbable material or a non-absorbable material. The medical textile material may comprise a polydioxanone, polycarbonate, polyurethane, poly(alpha-ester), polyglycolide, polylactide (e.g., poly(L-lactic acid), poly(D-lactic acid), and poly(D,L-lactic acid), poly (4-hydroxybutyric acid)—which is a homopolymer of 4-hydroxybutyrate (4HB), and belongs to a diverse class of materials called polyhydroxyalkanoates (PHAs)—and poly(lactide-co-glycolide)), polycaprolactone, polypropylene, polyester, poly(propylene fumarate), polyanhydride, polyacetal, polycarbonate (e.g., poly(trimethylene carbonate)), poly(ortho ester), polyphosphazene, polyphosphoester, polytetrafluoroethylene, polyethylene terephthalate, or any combination or co-polymer thereof. Polypropylene, polyester, and polyethylene are a preferred medical textile materials. Co-polymers or mixtures of such polymers may also be used, for example, as a way to modulate the properties of the medical textile, including to make the medical textile more or less capable of stretching, or more or less stiff, or stronger or weaker, or for long-term, mid-term, or short-term potential for resorption/biodegradation.

The substrate material may comprise any suitable thickness, size, or dimensions. These properties may relate, in part, to the intended location of the substrate material once implanted in the body, as well as particular patient needs, condition, or characteristics. In some aspects, the substrate comprises a single layer. In some aspects, the substrate comprises a plurality of layers. The substrate may be three dimensional. In embodiments where the substrate is sewn (embroidered), one or more or the layers in a substrate comprising a plurality of layers may be sewn together in a first pattern.

The substrate material may comprise a film, preferably a biocompatible film. The film may comprise a layer placed on the outer surfaces of the substrate material, or the film may constitute the entire substrate material. The substrate material may comprise a coating or otherwise be impregnated with one or more therapeutic agents. For example, the substrate material may comprise an antibiotic or anti-inflammatory therapeutic agent.

The adhesion barrier is preferably incorporated as a layer onto the substrate material. The adhesion barrier may comprise a separate sheet, leaf, or layer that is sewn onto the substrate material or sewn into a layer of substrate material where the implant comprises more than one layer of substrate material. When the discrete attachment sites are stitches, these stitches may be sewn using a material that is also anti-adhesive.

The adhesion barrier may comprise any material that is suitable for implantation within a patient that has anti-adhesion properties or functionality. The adhesion barrier/anti-adhesion material may comprise chitosan, collagen, hyaluronic acid, icodextrin, fibrin, poly(L-lactide-co-D,L-lactide)/polylactic acid, polydioxanone, polytetrafluoroethylene, oxidized regenerated cellulose (ORC), a hydrogel, or any combination thereof. ORC is preferred. A hydrogel may comprise a self-healing hydrogel scaffold. The adhesion barrier/anti-adhesion material may be in the form of a scaffold, mesh, film, sheet, leaf, membrane, filament, thread, yarn, or other form suitable for inclusion as a layer that is sewn/embroidered onto or sewn/embroidered into a substrate material.

The adhesion barrier material may be resorbable by the body. In some aspects, the adhesion barrier material is substantially resorbed by the human body by about three weeks following implantation of the implant within the human body. In some aspects, the adhesion barrier material is substantially resorbed by the human body by about one month following implantation of the implant within the human body. In some aspects, the adhesion barrier material is substantially resorbed by the human body by about six weeks following implantation of the implant within the human body. In some aspects, the adhesion barrier material is substantially resorbed by the human body by about two months following implantation of the implant within the human body. In some aspects, the adhesion barrier material is substantially resorbed by the human body by about six months following implantation of the implant within the human body. In some variations the adhesion barrier (anti-adhesive material) is not absorbed by the body.

An adhesion barrier in the form of a mesh, sheet, leaf or membrane may have any suitable dimensions (e.g., 1×w), and may have any suitable thickness. A plurality of sheets may be used (which sheets may, but need not be, joined together, for example, with an adhesive or by sewing sheets together, or may be unjoined until they are all attached to the substrate) in order to enhance the thickness and/or the duration of adhesion inhibition within the body. An adhesion barrier may be colored. Colors may be used to indicate a proper orientation of the substrate for implantation, for example, or may indicate a front or back.

A filament, yarn or thread that is used sew an adhesive barrier onto a substrate may comprise any suitable material, including any adhesion barrier material described or exemplified herein. The filament, yarn, or thread, whether or not it comprises an adhesion barrier material, may comprises a non-bioabsorbable or a biodegradable/bioresorbable material, including any such material suitable for use as a medical textile as described or exemplified herein. Preferred materials may include, without limitation, ORC, polyglycolic acid, polylactic acid, polydioxanone, or any combination thereof.

A filament, yarn or thread used to stitch/embroider an adhesive barrier (anti-adhesive material) into or onto a substrate may comprise any suitable weight. The yarn or thread may comprise monofilament yarn or thread, or multifilament yarn or thread. The thread weight may range from about 20 weight to about 120 weight. The thread may comprise a denier of from about 1 denier to about 2000 denier. The thread may comprise a denier of at least about 20-denier. The thread may comprise a denier of at least about 30-denier. The thread may comprise a denier of at least about 40-denier. The thread may comprise a denier of at least about 50-denier. The thread may comprise a denier of at least about 60-denier. The thread may comprise a denier of at least about 70-denier. The thread may comprise a denier of at least about 80-denier. The thread may comprise a denier of at least about 90-denier. The thread may comprise a denier of at least about 100-denier. The thread may comprise a denier of at least about 120-denier. The thread may comprise a denier of at least about 150-denier. The thread may comprise a denier of at least about 200-denier. The thread may comprise a denier of at least about 250-denier. The thread may comprise a denier of at least about 300-denier. The thread may comprise a denier of at least about 400-denier. The thread may comprise a denier of at least about 500-denier. The thread may comprise a denier of at least about 600-denier. The thread may comprise a denier of at least about 700-denier.

For example a yarn of an anti-adhesion material may be used and may comprise plied yarn or twisted yarn (e.g., z twist or s twist), or may comprise a braided yarn. The thread of an anti-adhesion material may comprise a continuous filament. The thread of an anti-adhesion material may comprise a staple filament. The filament, yarn or thread may be colored. Colors may be used to indicate a proper orientation of the substrate for implantation, for example, or may indicate a front or back.

The combination of a substrate and adhesion barrier, whether the barrier is sewn onto or sewn into the substrate (e.g., the substrate-barrier unit), may be used in a surgical implantation procedure, for example, for purposes of soft tissue repair or regeneration such as a hernia repair. Once the substrate-barrier unit is implanted within the patient's body, the adhesion barrier serves to inhibit adhesion formation, at least between the substrate and adjacent tissue or organs in the body.

An adhesion barrier layer (e.g., sheet) may be sewn onto the substrate, forming a plurality of discrete attachment sites corresponding to the stitches between the two layers. The adhesion barrier layer may be sufficiently flexible (compliant) so as not to stiffen the substrate material or restrict the intended and natural flexibility of the substrate within the body, less the substrate-barrier unit cause discomfort within the patient. The stitching pattern that joins the adhesion barrier layer to the substrate material can be selected to allow the adhesion barrier layer to move and flex with the movement and flexing of the substrate, particularly when implanted. Relative movement among layers of the substrate-barrier unit permits bending and pliability of the substrate-barrier unit, for example, in order to compensate for any reduction in flexibility caused by multiple layers increasing the thickness of the substrate-barrier unit. For example, the stitching type, stitching pattern, stitching density, and stitching location(s), as well as the stitch density and number of stitches may modulate flexibility and capacity for movement, as well as provide for a more stable attachment between the adhesion barrier layer and the substrate. The filament, thread, or yarn preferably comprises an adhesion barrier material such as ORC. Where the discrete attachment sites are formed by an adhesive rather than or in addition to a stitch, the same considerations list above for stitching may apply (e.g., attachment pattern, attachment density, attachment location(s), etc.).

The adhesion barrier layer (e.g., sheet) may be joined to the substrate material in a way that the adhesion barrier layer is more freely movable (e.g., slideable) or flexible relative to the substrate material, and/or relative to the different layers of a substrate material where the substrate material comprises a plurality of layers. The capacity of the adhesion barrier to move may relate to the stitching pattern, as well as aspects of stitching such as the density or number of stitches, angles of the stitch pattern, stitch direction, and the overlay of one or more stitch patterns, as well as the placement and relative tightness or looseness of how the stitches are laid.

After the adhesion barrier layer and substrate material are joined together, it may be necessary or desired to trim or cut the substrate-barrier unit, for example, in order to reduce its size or to conform to a desired shape. For example, such size or shape adjustments may be to accommodate the needs or situation of the patient into which the substrate-barrier unit is implanted. Thus, it is highly preferred that the stitching pattern used to join the adhesion barrier layer and the substrate together is laid in a way (e.g., at a sufficient density (e.g., relatively high density sewing), number of thread interlace points, etc.) that allows the remaining substrate-barrier unit to remain joined together without delaminating, or without having loose severed ends of threads hanging off of the cut points on the substrate-barrier unit.

The stitching pattern to join an adhesion barrier (e.g., sheet(s)) to the substrate material may constitute a single stitch pattern or a combination of stitch patterns. The type of stitch may include a chain stitch, Merrow stitch, lock stitch, zigzag stitch, straight stitch, running stitch, back stitch, satin stitch, or combinations thereof. Any of these stitching types or patterns may be used to form the embroidered pattern on the substrate as well.

Figure 2B:
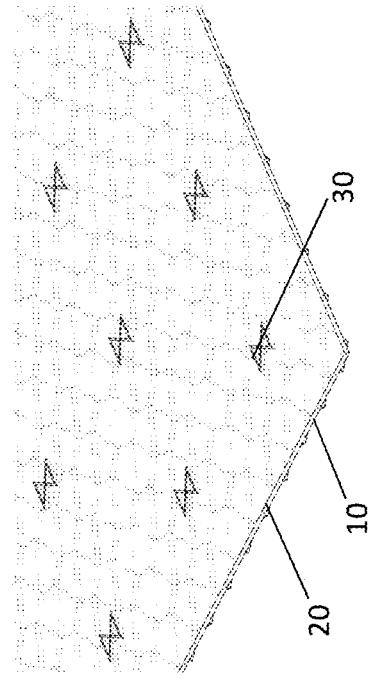
FIGS. 2A through 2G show different stitch patterns for the discrete attachment sites (stitches) that may be used to join an adhesion barrier to a mesh substrate to form a substrate-barrier unit.
Figure 2D:
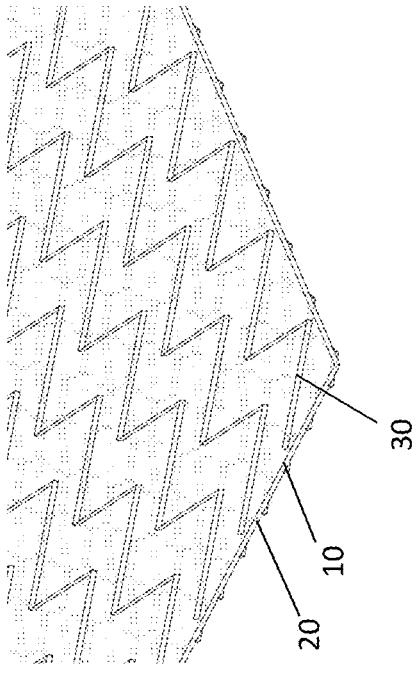
Figure 2A:
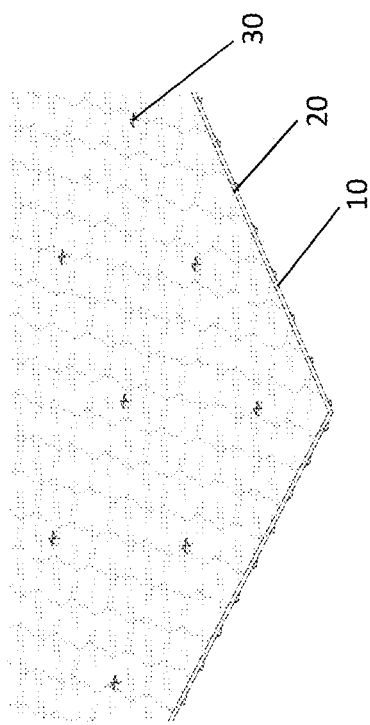
Figure 2C:
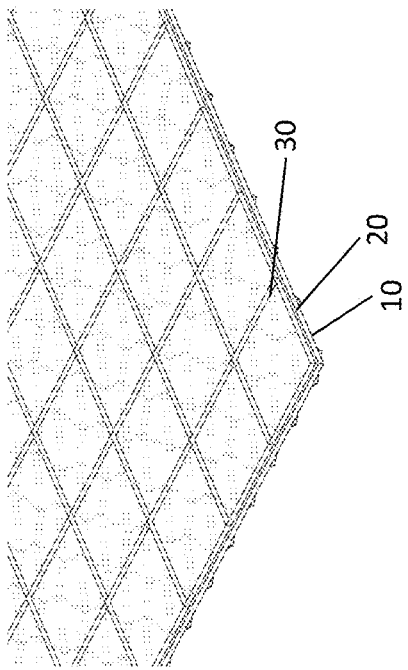
Figure 2F:
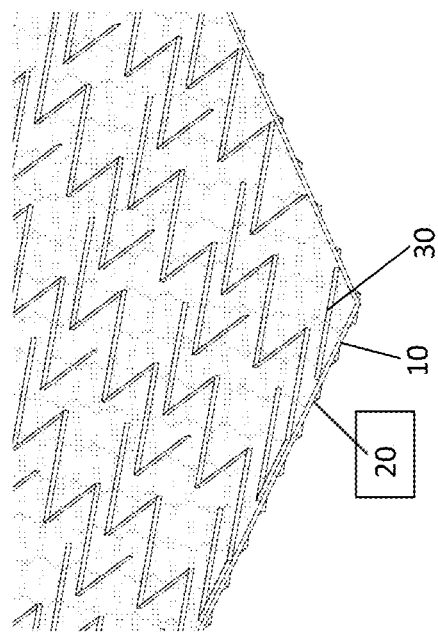
Figure 2G:
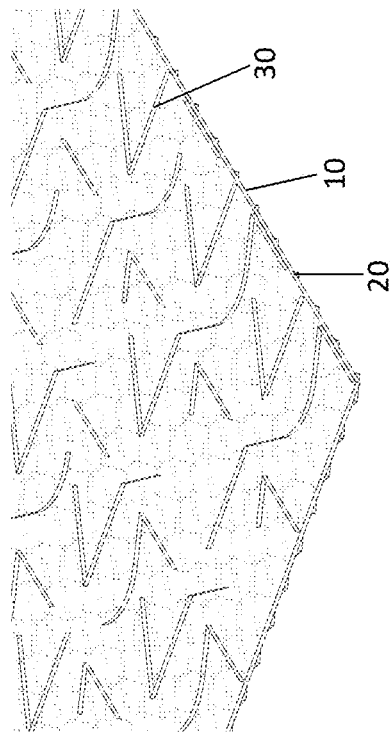
Figure 2E:
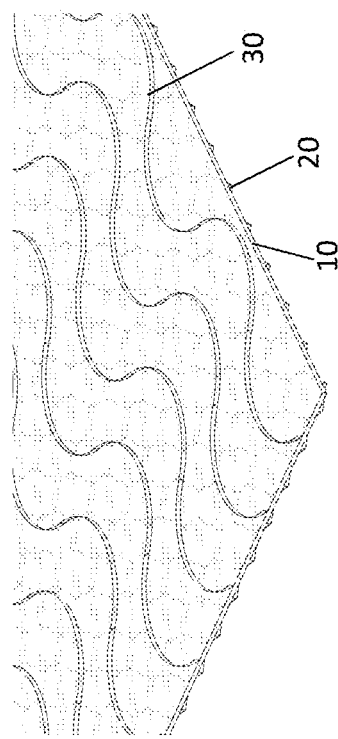

The stitching pattern to join an adhesion barrier (e.g., sheet) to the substrate material may comprise one or more straight lines. The stitching pattern to join an adhesion barrier (e.g., sheet) 20 to the substrate material 10 may comprise island stitches 30, whereby stitches are laid at certain points in the substrate and the adhesion barrier sheet (the islands), with spaces in between having no stitching (FIG. 1, FIG. 2A, and FIG. 2B). FIG. 2A shows an example of a small island stitch pattern 30 and FIG. 2B shows an example of a large island stitch pattern 30. Where a plurality of straight lines are employed, they may be sewn/embroidered in parallel, including in a grid pattern 30 (FIG. 2C), or they may be sewn/embroidered or in a straight or a zig-zag configuration 30 (FIG. 2D), or they may be sewn/embroidered in a configuration comprising a plurality of curves such as waves, oscillating lines, ripples, undulations, and other forms of curves (FIG. 2E). The stitching pattern may also comprise interrupted patterns (e.g., interrupted straight lines, interrupted curves, interrupted zig-zags, and interruptions of other patterns described or exemplified herein, or otherwise known), with a non-limiting example of an interrupted zig-zag shown in FIG. 2F. The stitching pattern may also comprise random patterns, a non-limiting example of which is shown in FIG. 2G.

Figure 3:
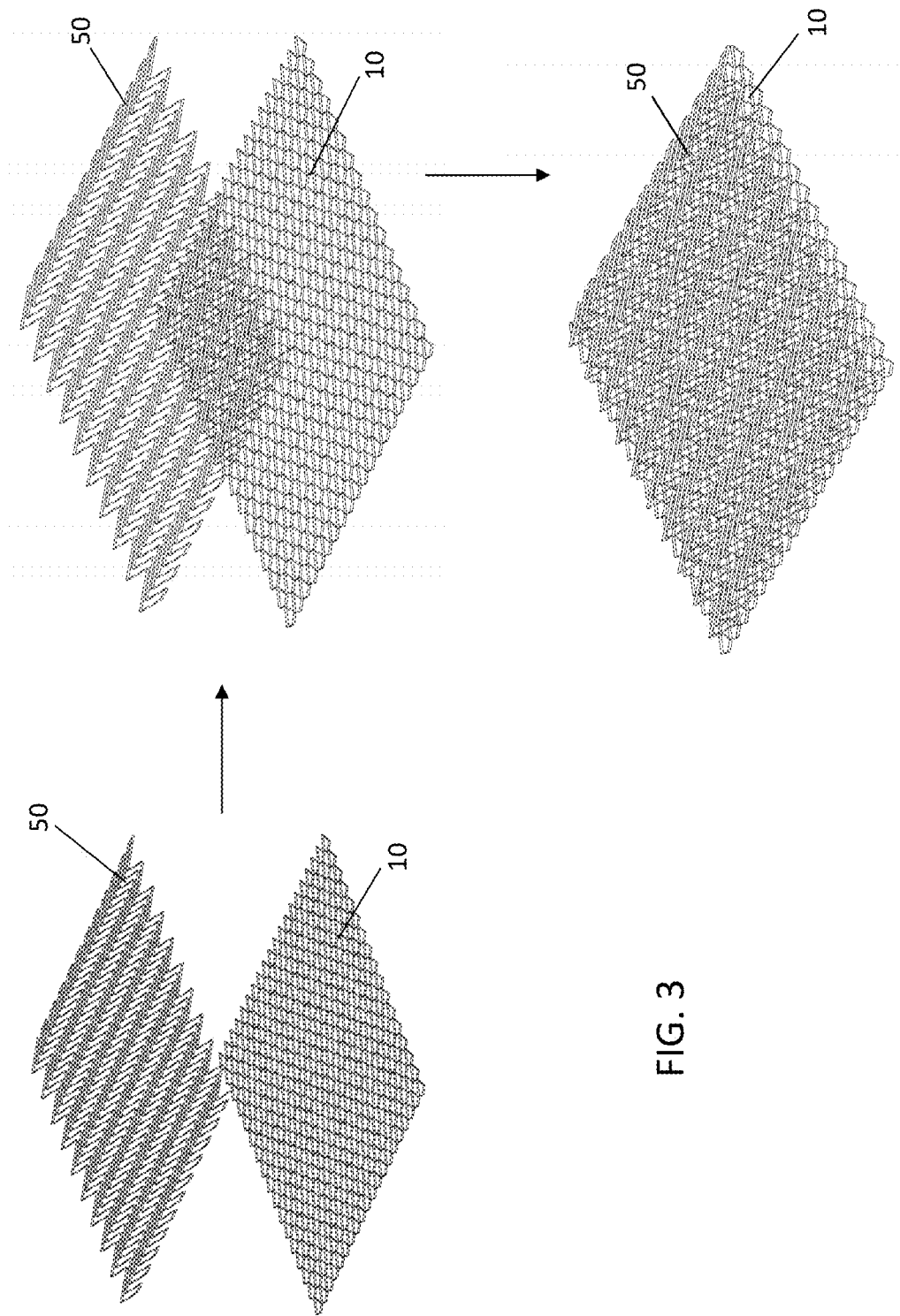
FIG. 3 shows an example of a first pattern embroidered onto a mesh substrate.

In any of the apparatuses described herein (including the grafts, etc.) a reinforcing embroidered pattern may be sewn into the substrate material. See, for example, FIG. 3. In this example, threads or yarns 50 (which may be an adhesion barrier material) may be are sewn or embroidered into the substrate material 10. The embroidered threads (fibers, etc.) may form a layer that is integral with the substrate material (FIG. 3, third panel), and connected to the substrate material at numerous thread interlace points (e.g., FIG. 4A) established where the sewing needle punctures the substrate material and the threads or yarns are intertwined together by the coordination of the sewing needle (for an upper thread/yarn) and bobbin/bobbin driver (for a lower thread/yarn). Each stitch may comprise one or more, e.g., at least two threads, yarns, or filaments—e.g., an upper thread and a lower thread, which each are sewn into the substrate material. In some variation, where the embroidered pattern is sufficiently dense, an additional anti-adhesion layer is not needed; however, in general, an adhesion barrier is preferably attached (flexibly attached) to the substrate material. Sewing or embroidery may be by hand, by machine, or any combination thereof. Sewing may be with a ballpoint needle.

As mentioned, the addition of the embroidered pattern of material (e.g., typically a bioabsorbable material or a material having a greater bio-absorption than the substrate/mesh) may decrease the compliance of the substrate. In the apparatuses described herein it has been found to be of particular medical benefit to use a substrate (e.g., mesh) having a compliance that is greater than the range of compliances identified as most beneficial for soft tissue (e.g., hernia) repair, such as the range of between 10% and 30% compliance strain at 16N/cm (see, e.g., Deeken et al. (2011), Physiocomechanical evaluation of absorbable and nonabsorbable barrier composite meshes for laparoscopic ventral hernia repair. *Surg. Endosc.,* 25(5), 1541-1552). For example, the bare mesh may have a % compliance strain at 16N/cm of between 30% and 80%). The addition of the embroidered pattern, typically using a filament that is bioabsorbable in a pattern such as a grid pattern (or a plurality of overlapping, rotationally offset, grid patterns) may decrease the % compliance strain at 16N/cm to within the 10%-30% range or thereabouts (e.g., between 40%-10%).

Figure 4A:
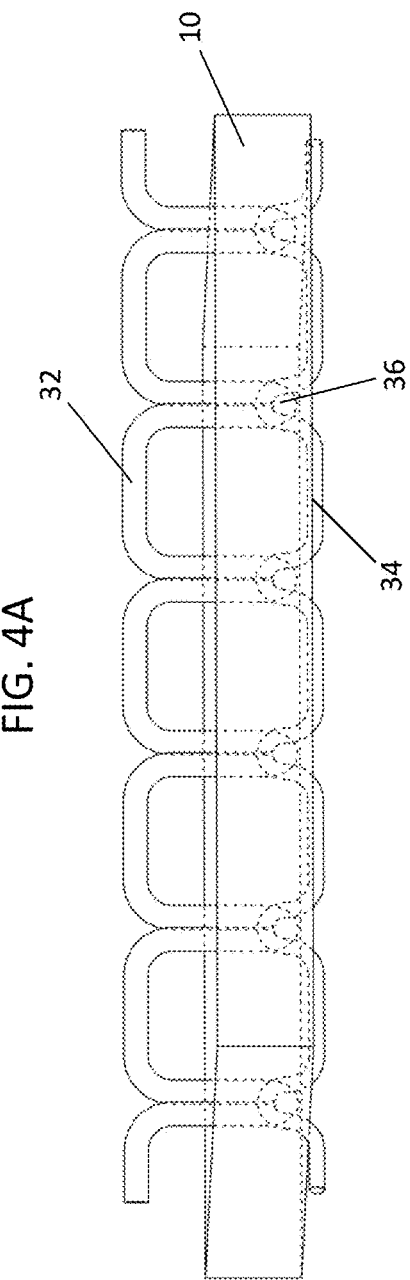
FIG. 4A shows a side view of threads (e.g., which may be made of an adhesion barrier material) sewn into a substrate; the lockstitch of the upper and lower threads is shown (dotted lines). The upper thread has a larger diameter relative to the lower thread in this example.
Figure 4B:
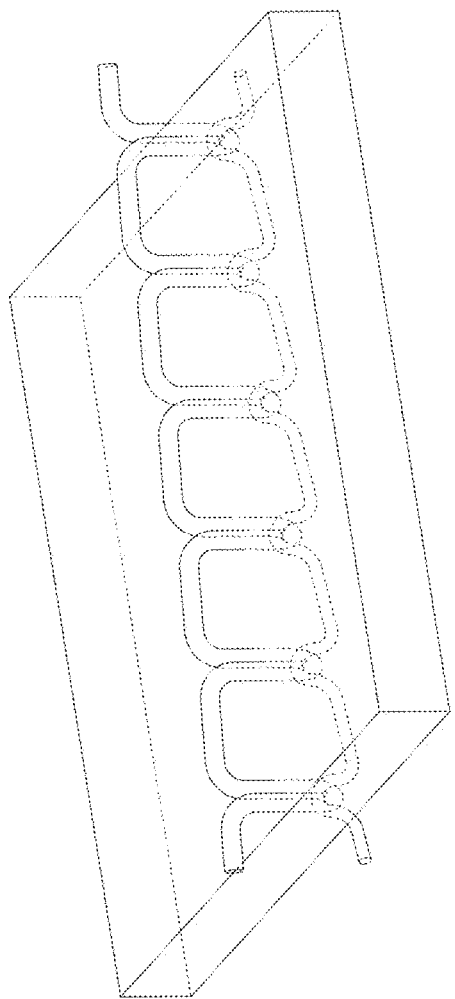
FIG. 4B shows an isometric perspective view of the embroidered substrate shown in FIG. 4A.

Filaments, threads, or yarns may be sewn in both the embroidered pattern on the mesh and/or the pattern connecting the substrate to the anti-adhesion layers may be any suitable stitch patterns. In some aspects, the material is sewn as a line, for example, as shown in FIG. 4A and FIG. 4B. For example, using a sewing machine, an upper thread 32 and lower thread 34 of adhesion barrier material may be sewn into the substrate 10. The upper thread 32 may have a larger diameter relative to the lower thread 34 (FIG. 4A), though the upper 32 and lower 34 threads may have substantially the same diameter relative to each other, or the lower thread 34 may have a larger diameter relative to the upper thread 32. The upper thread 32 and lower thread 34 may be joined at a thread interlace point 36, created by the sewing machine. A suitable diameter may be from about 0.001 inches (about 0.0025 mm) to about 0.05 inches (about 1.27 mm) for a monofilament or multifilament.

Figure 5A:
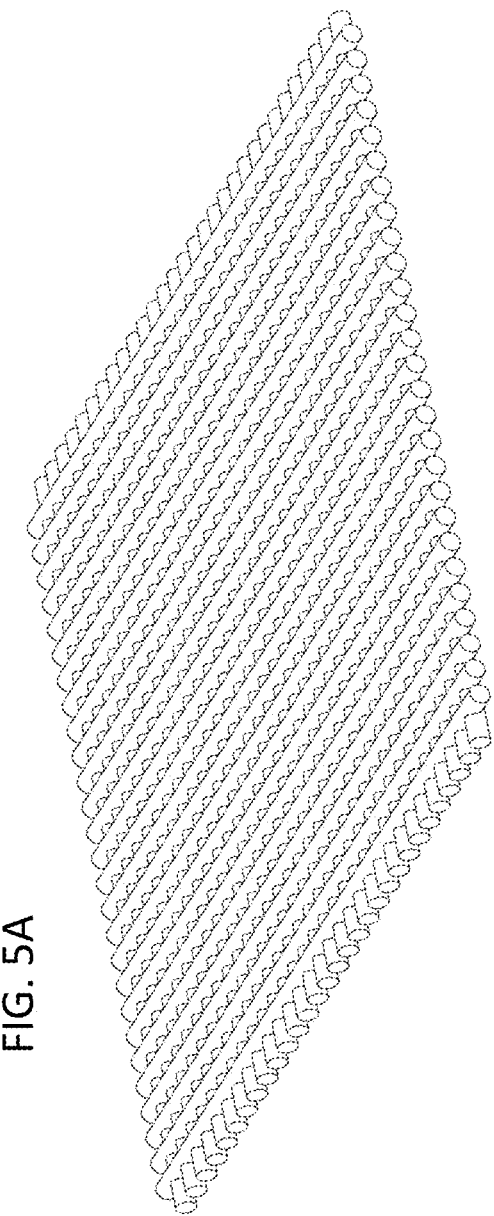
FIG. 5A shows a representation of a substrate mesh without any embroidered pattern.
Figure 5B:
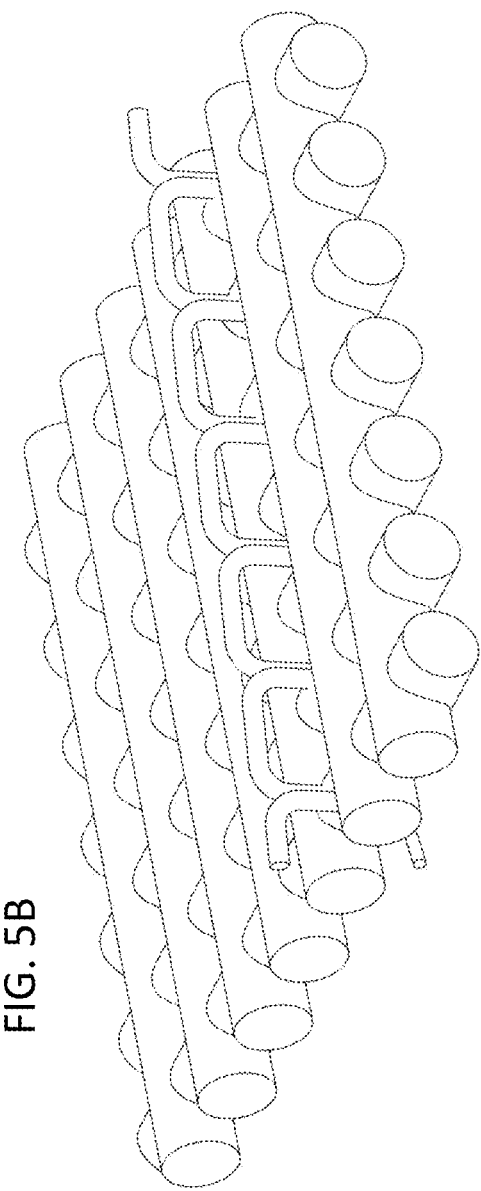
FIG. 5B shows a close-up view of the substrate from FIG. 5A into which threads (e.g., of an adhesion barrier material) have been sewn. The upper thread has a larger diameter relative to the lower thread.
Figure 5C:
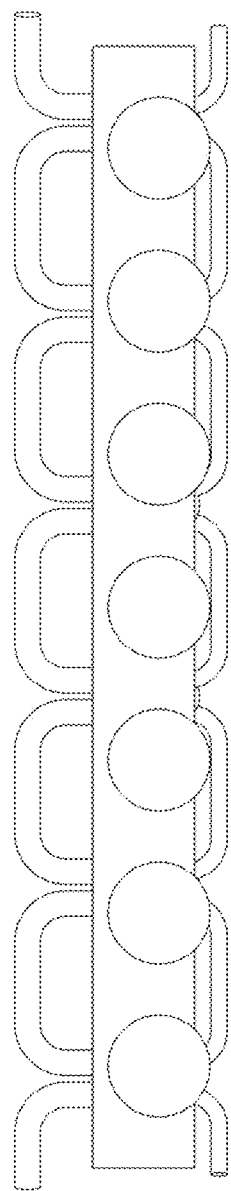
FIG. 5C shows a side view of the threads sewn into the substrate.
Figure 5D:
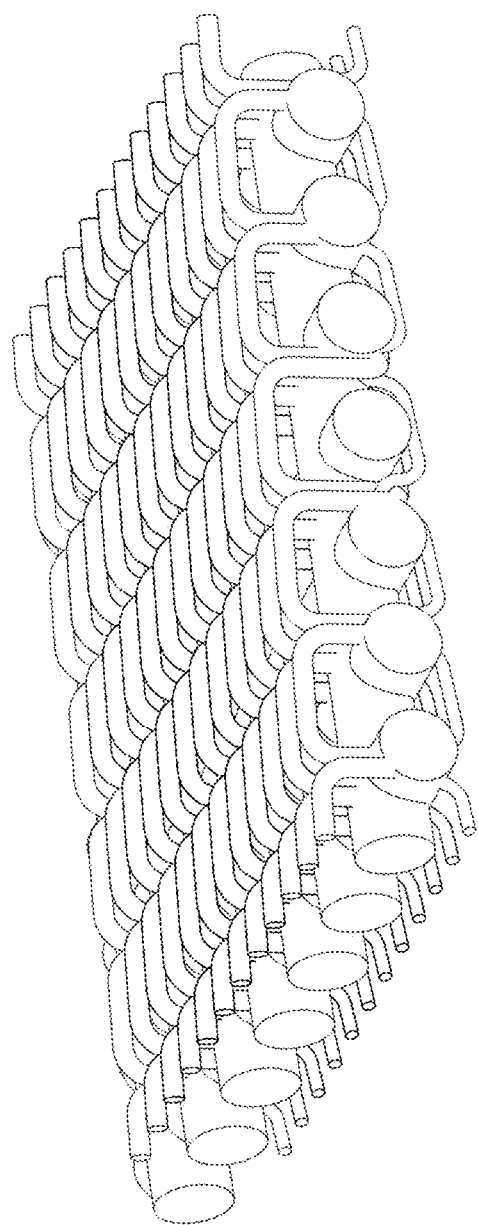
FIG. 5D shows a representation of the substrate fabric or mesh into which a high density of threads have been sewn.
Figure 5E:
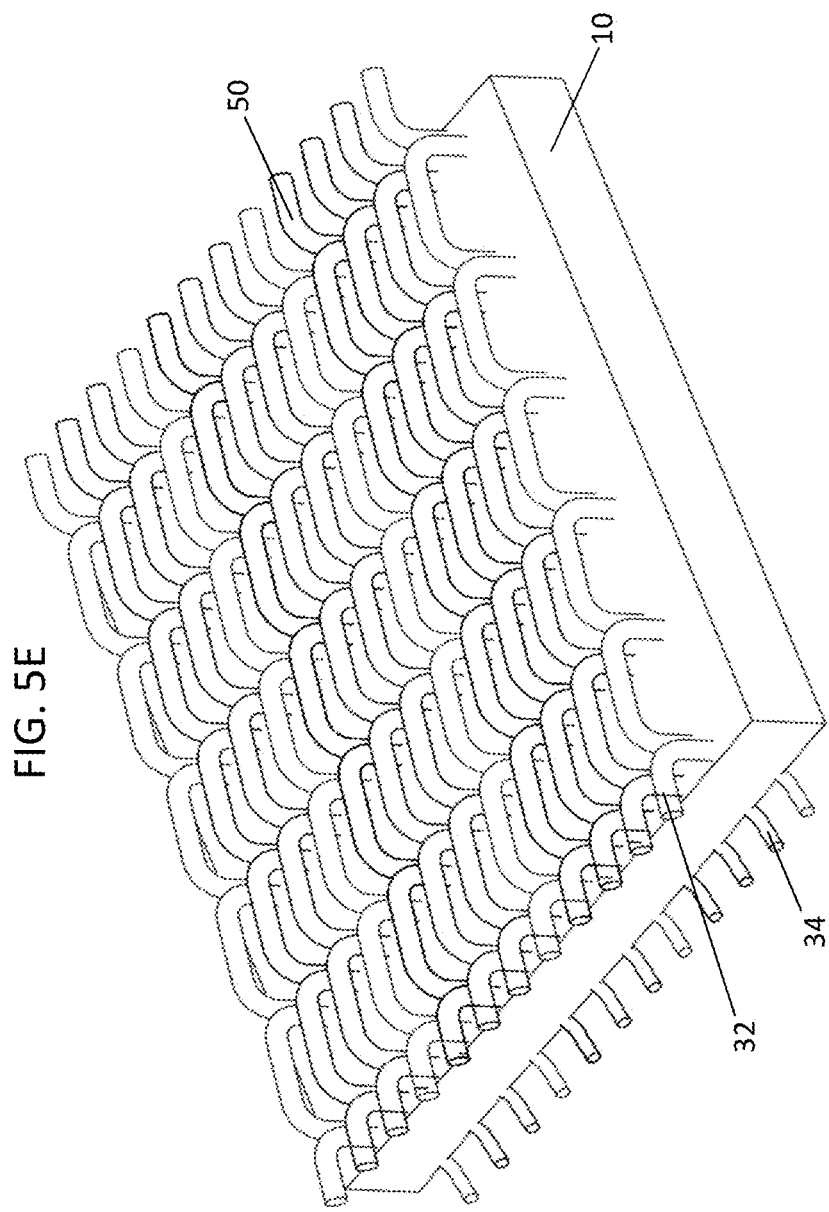
FIG. 5E shows a top perspective view of FIG. 5D.
Figure 6C:
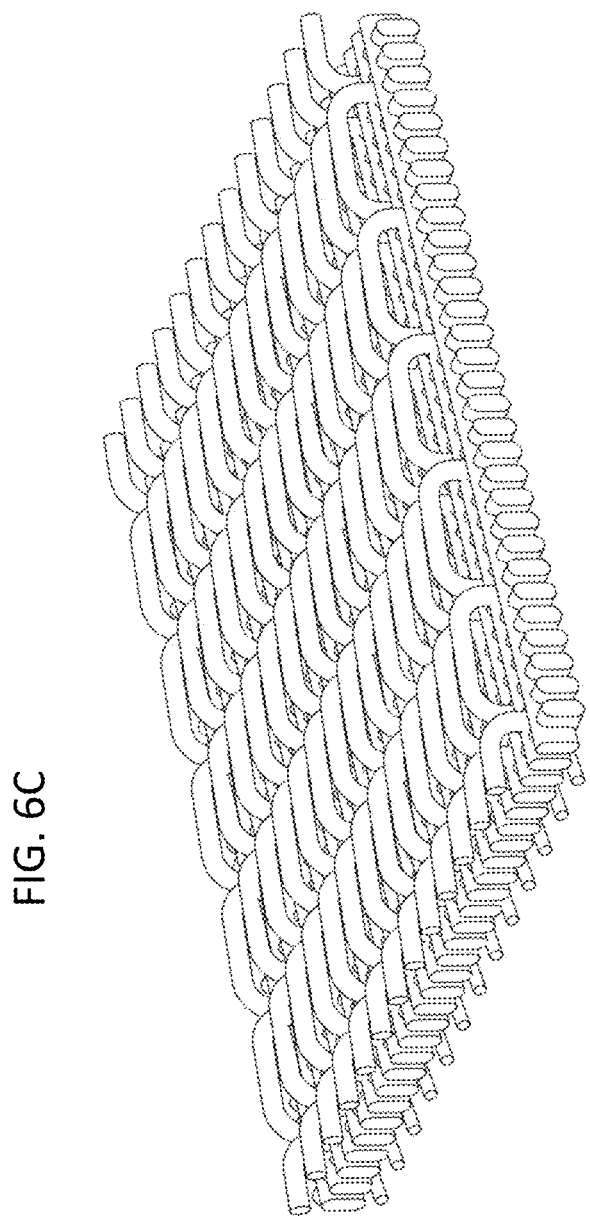
FIG. 6C shows a representation of the substrate fabric or mesh into which a high density of threads have been sewn.

The adhesion barrier materials may be attached to the substrate in a sewn pattern that is different from that of the embroidered pattern (which is typically a tighter, higher-density pattern). The embroidered pattern may be a pattern comprising a plurality of lines, including parallel lines (e.g., FIG. 5D, FIG. 5E, and FIG. 6C), or non-parallel lines that may, but need not, intersect with other sewn lines. The stitches may interlace between substrate fibers (fibers, for example, as shown in FIG. 5A), for example, as shown in FIG. 5B, FIG. 5C, FIG. 6A, and FIG. 6B. The stitched lines may comprise interruptions (e.g., breaks between lines such that the lines are not continuous) or may be continuous. The stitched lines may be staggered relative to other stitched lines.

Stitches and stitch patterns may be sewn (embroidered) into the substrate material at any suitable density. The density may provide for higher surface area coverage and, at least for a period of time, the density may also impart strength or reinforcement into the substrate. The stitching density may also make the substrate more resistant to stretching relative to a lower density of stitches. Density may comprise the number of stitches within a stitch pattern. Density may comprise the number of adjacent or parallel stitch patterns and/or the proximity of adjacent or parallel stitch patterns to each other or other stitch patterns (e.g., FIG. 5D, FIG. 5E, and FIG. 6C).

Figures 7A, 7B:
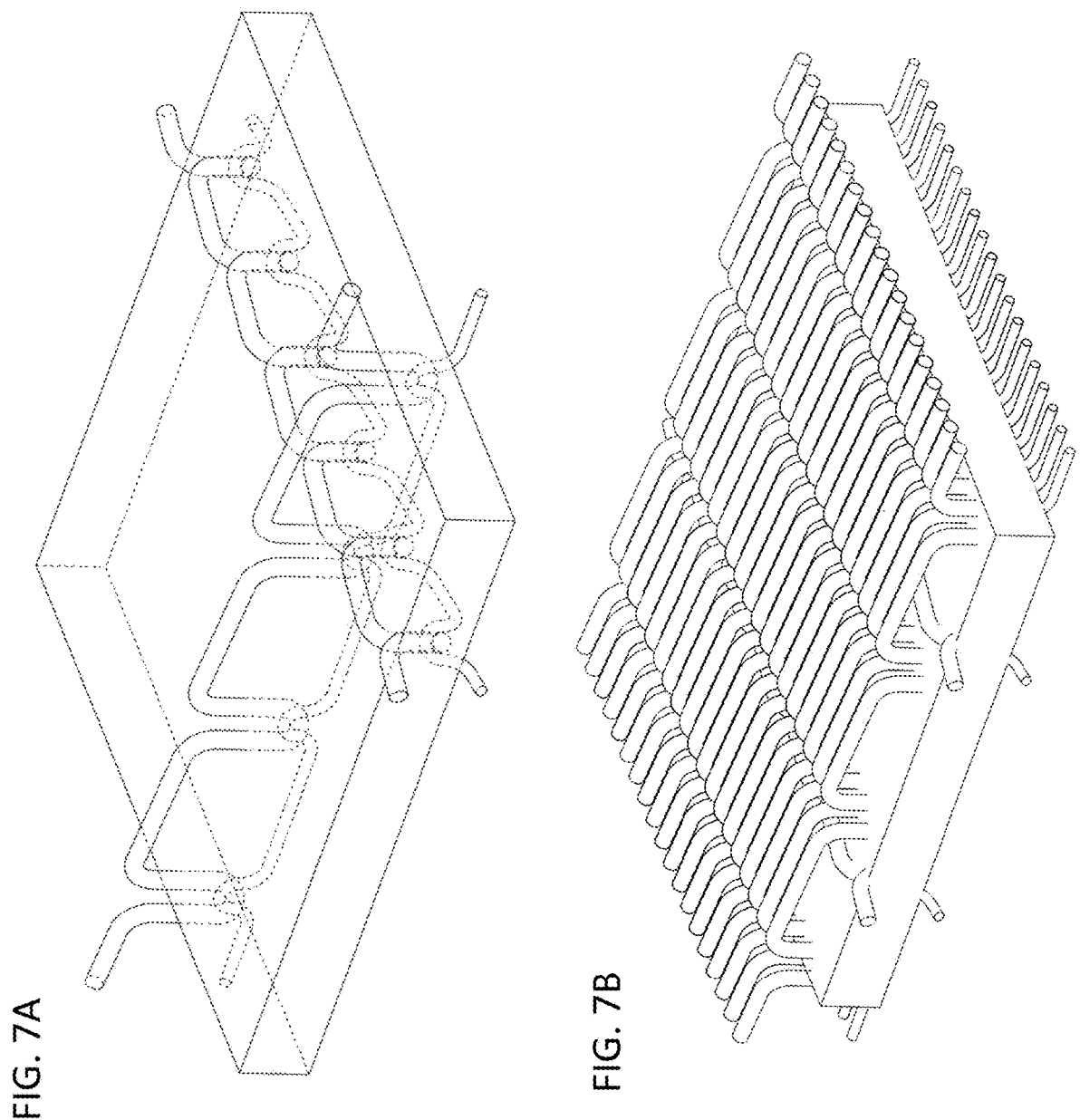
FIG. 7A shows a representation of a substrate material into which crisscrossing threads have been embroidered. In each pass of the embroidered threads, the upper thread has a larger diameter than the lower thread.
FIG. 7B shows a representation of the substrate fabric or mesh into which a high density of crisscrossing threads have been sewn.

Stitch patterns may be overlaid in either the embroidered pattern on the substrate and/or the pattern connecting the first and second layers (e.g., substrate and anti-adhesion layers). Thus, for example, a second stitch pattern (second sub-pattern) may be sewn or embroidered over a first stitch pattern (first sub-pattern). The filaments (threads, etc.) may be sewn into a pattern comprising a plurality of perpendicular or intersecting lines (e.g., FIG. 7A). Subsequent stitch patterns may be sewn in a different direction relative to another stitch pattern. Thus for example, a second stitch pattern may be sewn into the substrate material in a direction that is diagonal or perpendicular to the direction of another stitch pattern sewn into the substrate material. Each set of intersecting lines may be sewn into the substrate material at any suitable density. For example, one set of lines may be sewn at a relatively high density and another set of lines (the intersecting set) may be sewn at a relatively low density, for example, as shown in FIG. 7B. In some aspects, both sets of intersecting lines may be sewn at a high density (not shown). The high density line set may be sewn on top of the low density line set (FIG. 7B), or vice versa.

Stitch patterns may comprise parallel straight lines, non-parallel straight lines, intersecting lines, staggered lines, grids, random stitching, curves, angled lines, zig-zags, or any combination thereof, any of which may comprise irregular patterns, regular patterns, or a combination of regular and irregular patterns, and any of which may comprise continuous stitching, interrupted stitching, or a combination of continuous and interrupted stitching.

Figure 8B:
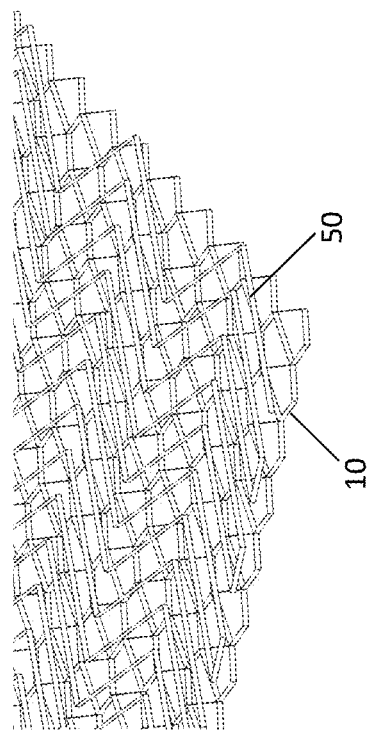
Figure 8D:
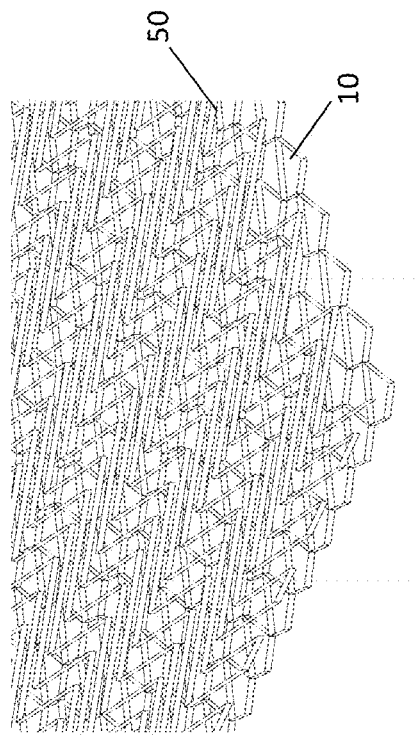
Figure 8A:
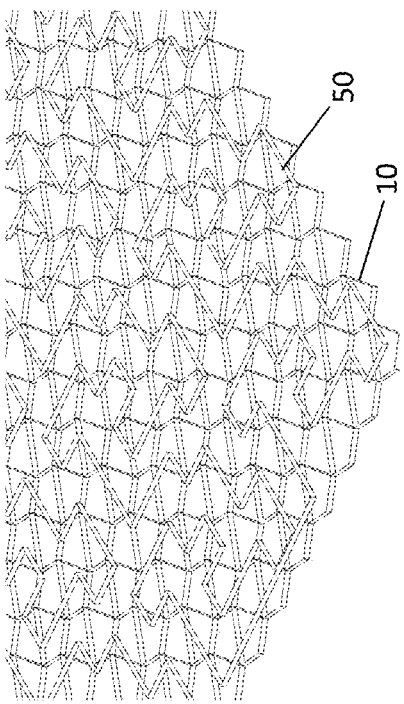
Figure 8C:
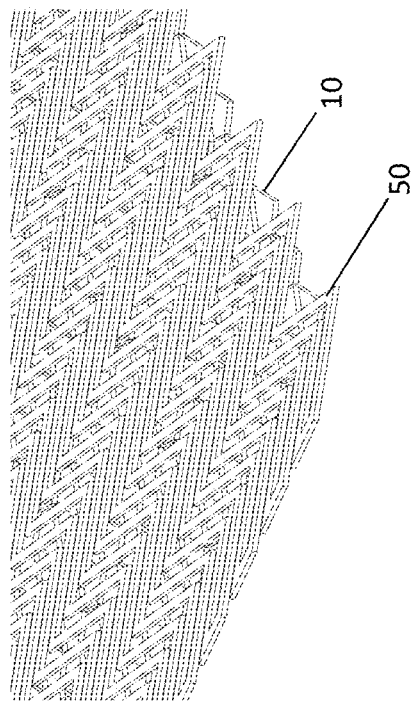
Figure 9A:
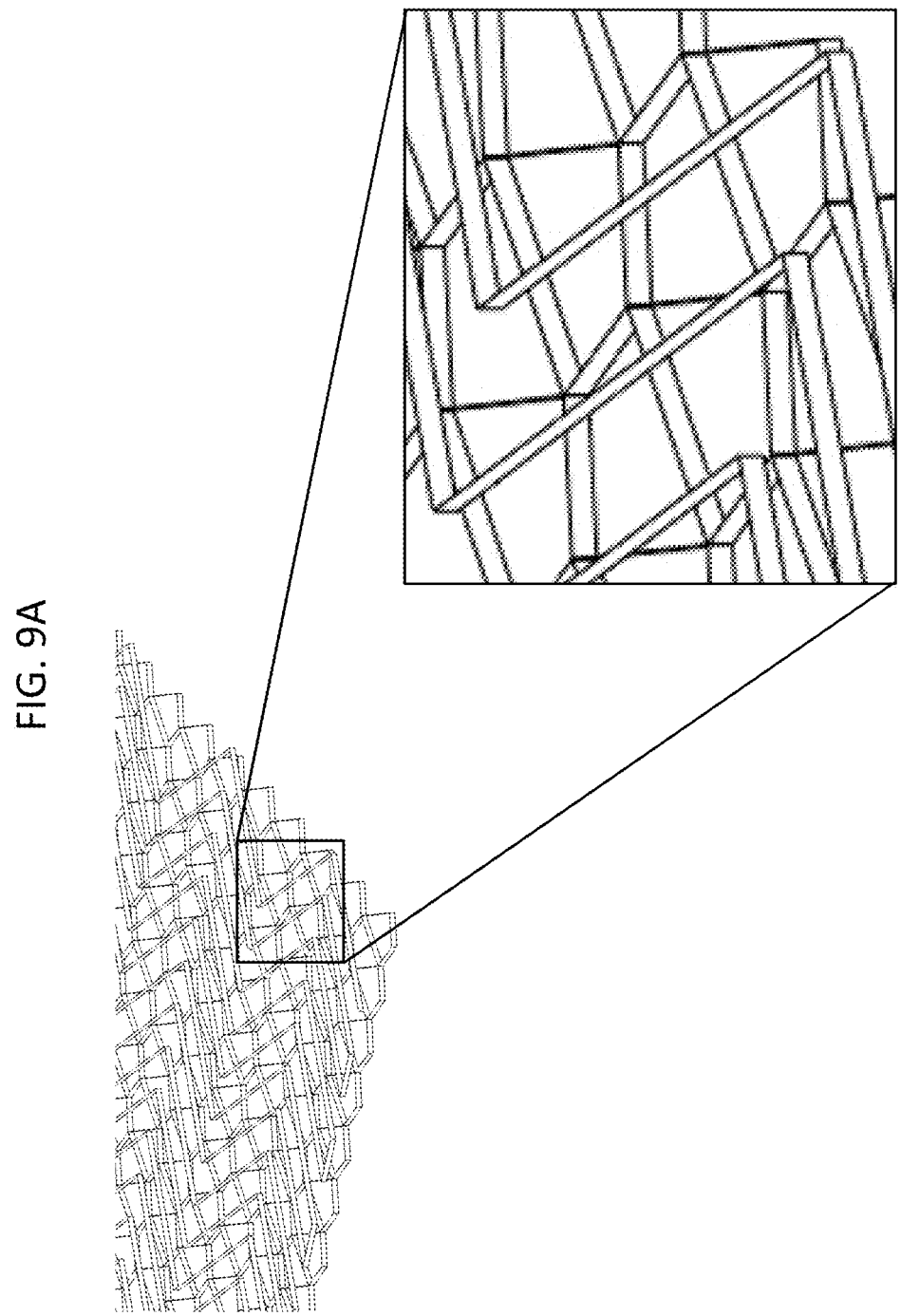
FIGS. 9A through 9D show an enlarged view of portions of the stitch patterns shown in FIGS. 8A through 8D. The expanded views show that the threads interlace about the mesh substrate.
Figure 9B:
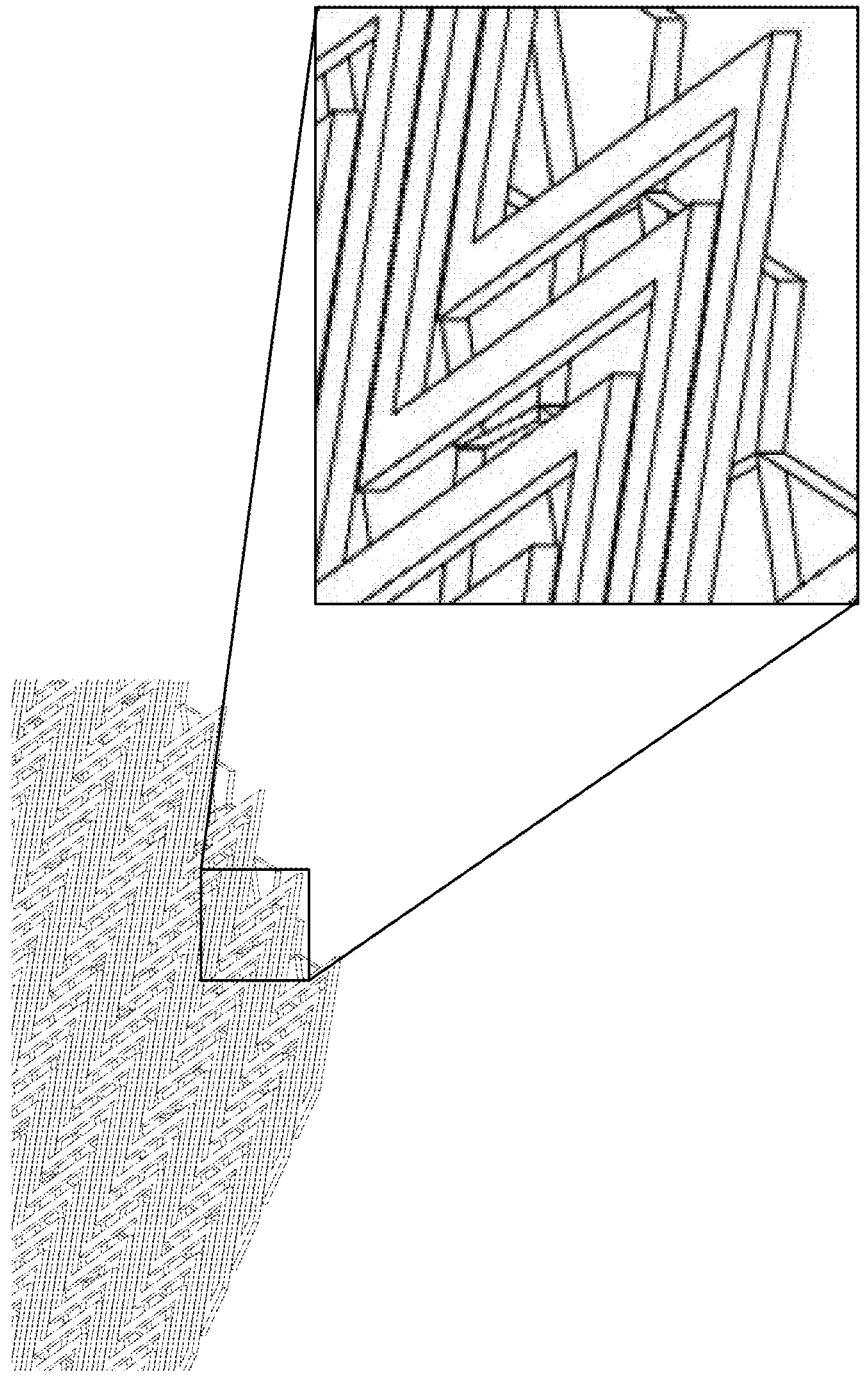
Figure 9C:
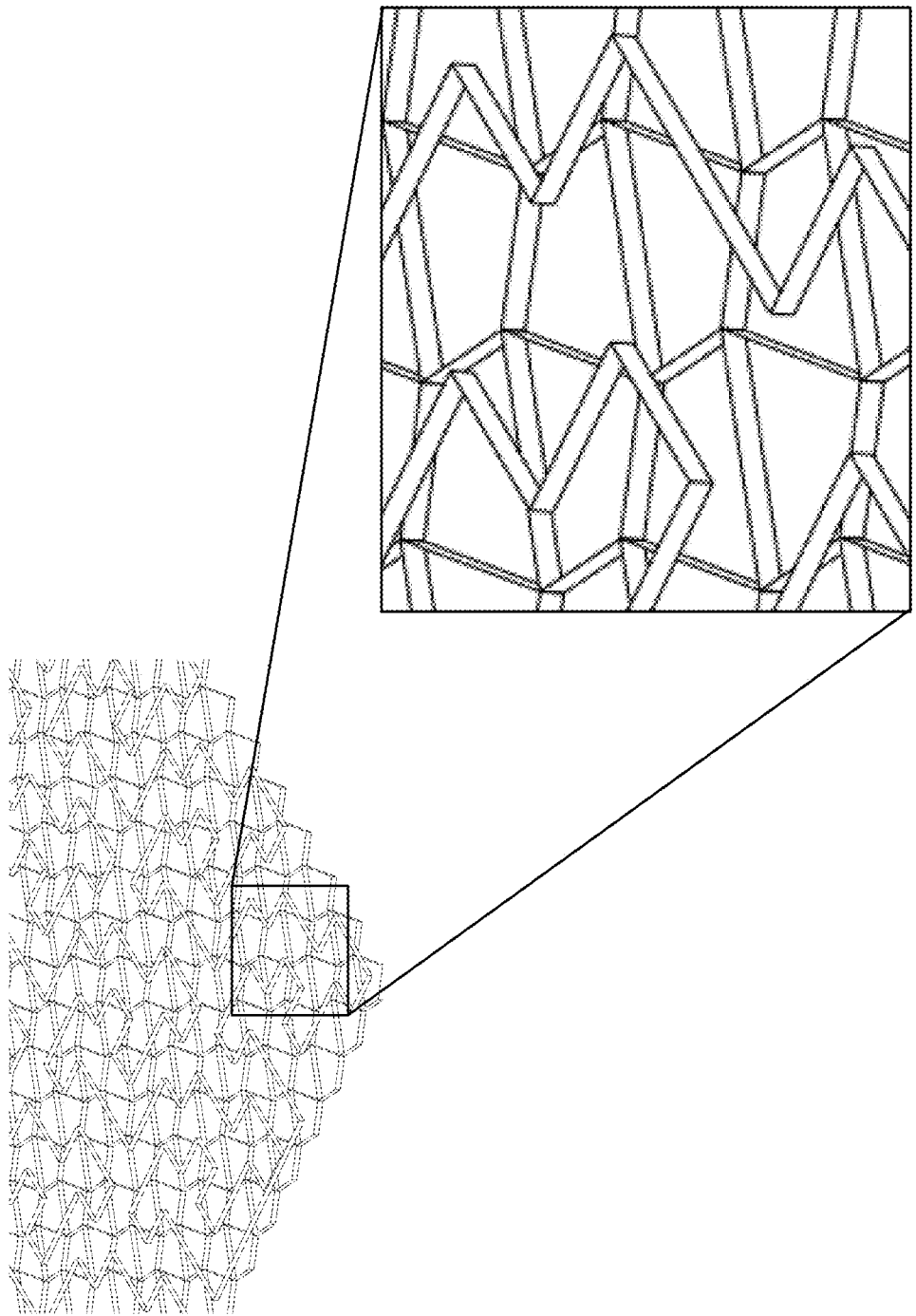
Figure 9D:
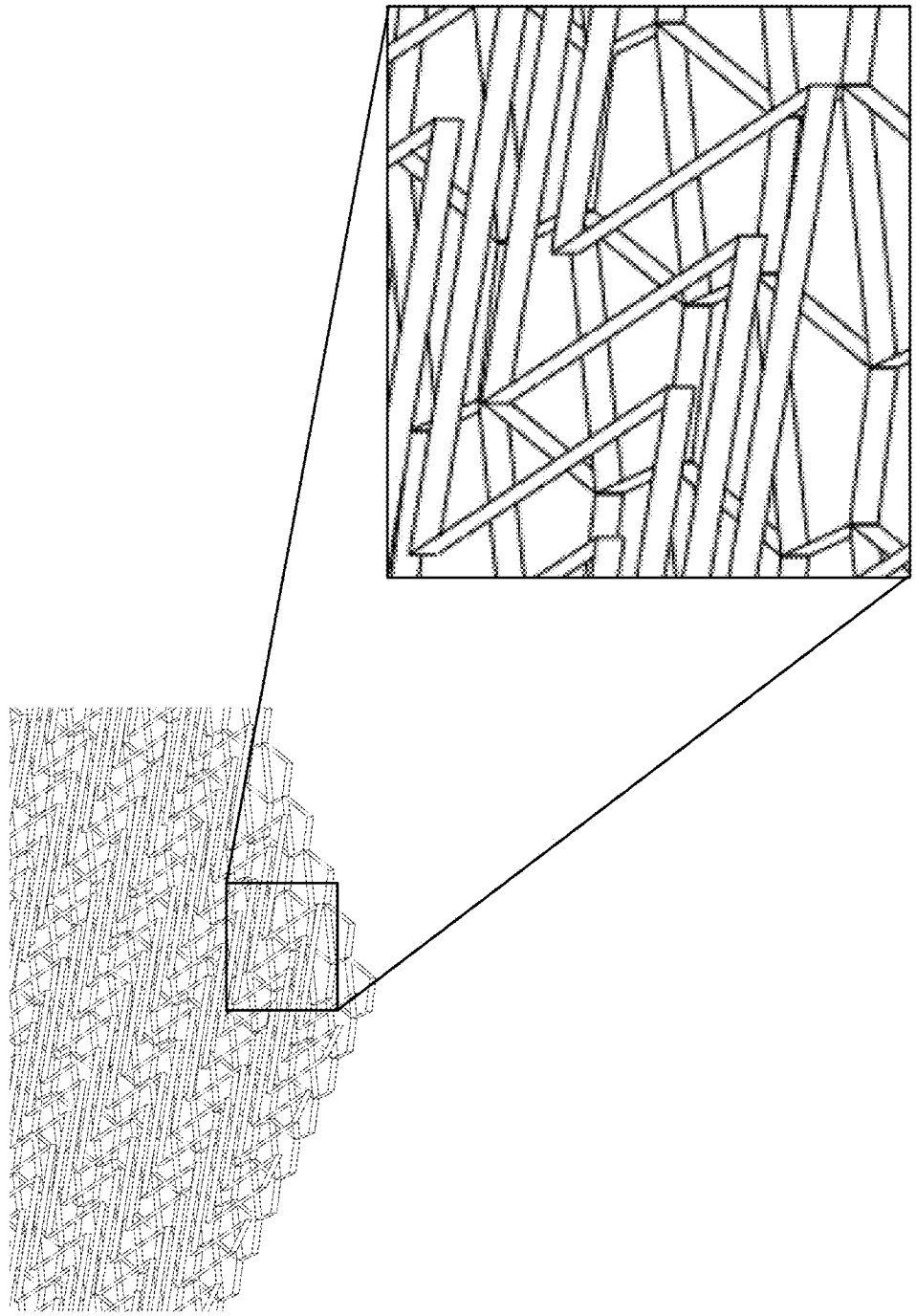

Zig-zag patterns may be preferred in some aspects, and each zig-zag may be sewn with different amplitudes and/or frequencies. FIGS. 8A through 8G show examples of suitable stitch patterns. FIG. 8A shows a squared stitch pattern, with threads 50 are sewn into the substrate 10 as a series of squares. FIG. 8B shows an example of a basic zig-zag pattern, with FIGS. 8C and 8D showing variations of a zig-zag pattern. In FIG. 8C, the zig-zag pattern is sewn at a high density and with larger-diameter threads. In FIG. 8D, the zig-zag pattern is sewn with different amplitudes and frequencies among the angled stitches. In FIG. 8E, a curved stitch pattern is sewn into the substrate material. In FIG. 8F, a stitch pattern comprising interrupted stitching is shown sewn into the substrate material, with the interrupted stitch pattern showing interrupted zig-zag stitches solely for illustration purposes, as any stitch pattern may comprise interruptions in the continuity of the stitches. In FIG. 8G, a random stitch pattern is shown sewn into the substrate material. FIGS. 9A through 9D show a close-up view of the patterns shown in FIGS. 8A through 8D, respectively, and illustrate that the threads interlace throughout the substrate in order to form the stitch pattern.

Stitch patterns may comprise a plurality of angles, which may comprise a plurality of repeating angles (FIGS. 8B to 8D). Where a plurality of angled lines is employed, they may be sewn/embroidered in parallel or in a grid pattern. The angle is formed between inflection points in the stitch pattern, and each angle may be from about 0 degrees to about 180 degrees, or at any integer between 0 degrees and 180 degrees, inclusive (e.g., 1 degrees, 2 degrees, 3 degrees, 4 degrees, 5 degrees, 6 degrees, 7 degrees, etc.). It is preferred that the same angle is used throughout a given stitch line, but in some aspects, a combination of different angles may be used throughout a given stitch line. Thus, by way of example and for illustration purposes only a stitch pattern may comprise a plurality of repeating 30 degree angles, or may comprise a plurality of alternating 30 and 50 degree angles, or may comprise any combination of angles.

Stitch patterns may comprise a plurality of lines arranged in a pattern comprising a plurality of curves, including a wave pattern, an undulating pattern, a ripple pattern, an oscillating line pattern, or any combination thereof, which may be regular or irregular. A subset of the lines in a curve pattern may comprise a different amplitude, frequency, or amplitude and frequency relative to another subset of the lines in a curve in the stitch pattern. When embroidering patterns onto the substrate, the embroidered pattern may be highly dense (e.g., covering more than 80%, 85%, 90%, 95%, 98%, 99%, etc. of at least the upper or lower surface of the substrate. Higher density patterns may be particularly helpful when an additional anti-adhesive layer is not applied.

In the case of parallel straight stitches or angled stitch patterns, placing such stitch patterns closer together allows for more stitch patterns to be sewn or embroidered into the substrate. High density parallel stitch patterns may comprise adjacent stitch patterns placed from about 0.5 mm to about 5 mm apart, may comprise adjacent stitch patterns placed from about 1 mm to about 4 mm apart, from about 1 mm to about 3.5 mm apart, from about 1 mm to about 3.3 mm apart, from about 1 mm to about 3.2 mm apart, from about 1 mm to about 3.1 mm apart, from about 1 mm to about 3 mm apart, from about 1 mm to about 2.8 mm apart, from about 1 mm to about 2.6 mm apart, from about 1 mm to about 2.5 mm apart, from about 1 mm to about 2.3 mm apart, from about 1 mm to about 2 mm apart, from about 2 mm to about 3.5 mm apart, from about 2 mm to about 3.3 mm apart, from about 2 mm to about 3.1 mm apart, from about 2 mm to about 3 mm apart, from about 2 mm to about 2.8 mm apart, from about 2 mm to about 2.5 mm apart, or from about 2 mm to about 2.2 mm apart.

Stitches may be from about 0.5 mm to about 12 mm per stitch. Stitches may be from about 1 mm to about 7 mm per stitch, from about 1 mm to about 6 mm per stitch, from about 1 mm to about 5 mm per stitch, from about 2 mm to about 6 mm per stitch, from about 2 mm to about 5 mm per stitch, from about 2 mm to about 4 mm per stitch, from about 3 mm to about 6 mm per stitch, or from about 3 mm to about 5 mm per stich.

In some aspects, the adhesion barrier material (e.g., threads, etc.) may be sewn into the substrate in a corner-locked stitch pattern. Such patterns are described in in U.S. patent application Ser. No. 15/196,439, incorporated by reference herein.

A stitch patterns may be sewn or embroidered through all layers of a layered substrate material. In some aspects, combinations of different stitch patterns may be sewn or embroidered into different portions of the substrate material, for example, to accommodate the direction or orientation or site of implantation.

Anti-Adhesive Materials (Layer 2)

Any of the anti-adhesive materials may be a biologic such as a sheet or sheets of ECM. For example, the sheet of anti-adhesive material may be a sheet of extracellular matrix derived from one or more of the dermis, pericardium, peritoneum, intestine, stomach, or forestomach.

Other adhesion barrier materials may include oxidized regenerated cellulose (ORC). ORC is typically produced by oxidizing the cellulose by exposing the cellulose to nitrogen dioxide or nitrogen tetroxide. See, for example, U.S. Pat. No. 3,364,200. Thus, an adhesion barrier in the form of a sheet, leaf or membrane preferably comprises ORC, such that the cellulose is already in oxidized form when the barrier is joined to the substrate as a substrate-barrier unit.

ORC in the form of a thread, yarn, or filament may be used to sew an adhesion barrier to the substrate and/or to embroider the substrate. Thus, the adhesion barrier material may be sewn to the substrate already in oxidized form. A thread, yarn, or filament of non-oxidized cellulose (e.g., rayon) may be used to sew to the substrate, particularly where the non-oxidized form may better withstand the forces applied by a sewing machine relative to the oxidized form. A stitch pattern as described or exemplified herein of the cellulose in non-oxidized form may be sewn into the substrate, and then the substrate and the stitches may be oxidized according to any suitable technique such that ORC results, thereby imparting adhesion barrier properties into the stitch pattern.

Figure 10A:
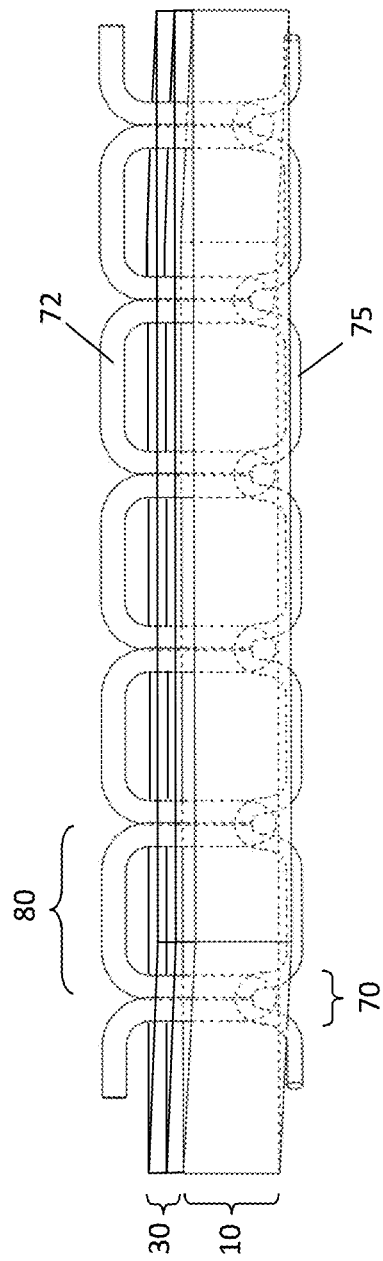
FIG. 10A shows a side view of threads (e.g., which may be made of an adhesion barrier material) sewn through both a substrate (e.g., mesh) and an adhesion barrier (e.g., ECM). In this example, the threads are shown passing through both layers forming a series of discrete attachment sites connecting the adhesion barrier and the substrate. A line of discrete attachment sites is formed. In this example, the adhesion barrier layer comprises two ECM layers. The adhesion stitching pattern shown comprises a lockstitch of an upper and lower thread. In this example, the upper thread has a larger diameter relative to the lower thread.
Figure 10B:
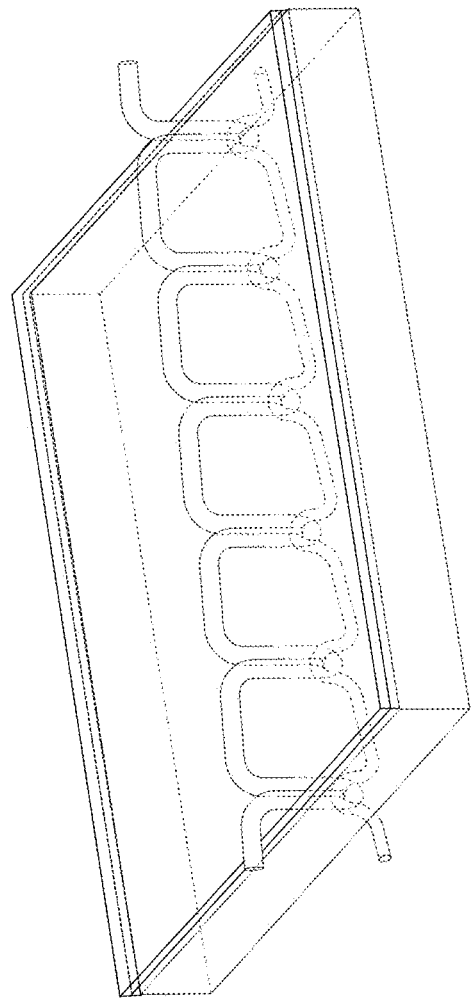
FIG. 10B shows an isometric perspective view of FIG. 10A.

FIG. 10A illustrates an example of a portion of a material (such as a graft material) formed as described herein. In this example, the anti-adhesive layer 30 is shown on the top and includes two (thorough one or more than two sheets may be used) sheets. The sheets are sewn into the substrate (e.g., a mesh) using a pair of threads 72, 75 that interlock. The resulting stitching pattern forms a plurality of discrete attachment sites 70. In this example, the discrete attachment sites in the line of stitches are separated from each other by a distance 80. The stitching pattern may extend along the outer surfaces of the material, and may form an overall attachment pattern such as a grid or any of the other patterns described herein. The attachment pattern flexibly secures the layers together. When a closed-cell pattern is formed (as shown by the grid patterns of FIG. 2C, the openings between the grids may have a minimum distance of between about 0.5 mm and 30 mm (e.g., between about 1 mm and 30 mm, between about 2 mm and 30 mm, between about 3 mm and 30 mm, between about 5 mm and 30 mm, etc.). When an open-cell pattern (e.g., parallel lines, discrete islands, random patterns), the openings between lines of stitching may have a minimum distance of between about 0.5 mm and 30 mm (e.g., between about 1 mm and 30 mm, between about 2 mm and 30 mm, between about 3 mm and 30 mm, between about 5 mm and 30 mm, etc.).

Figure 11B:
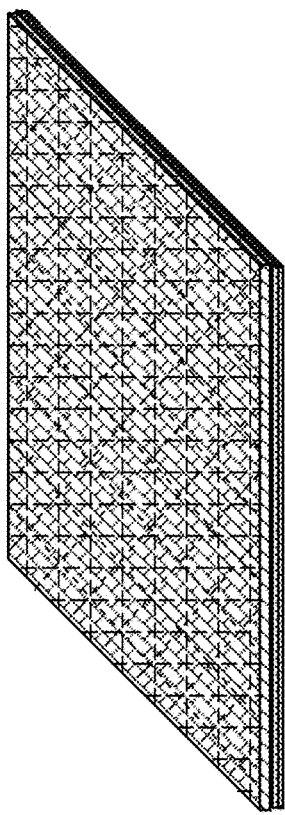
FIG. 11B shows a view of a first side of the graft (mesh side), showing the layers stacked and attached in a pattern of discrete stitched attachment sites, formed by stitching in this example.
Figure 11C:
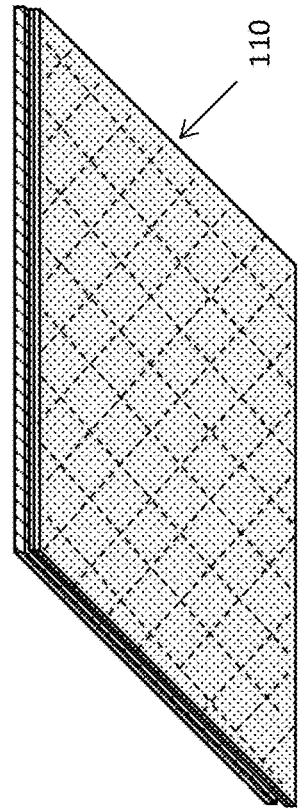
In FIG. 11C the opposite side of the graft (ECM side) is shown.
Figure 11A:
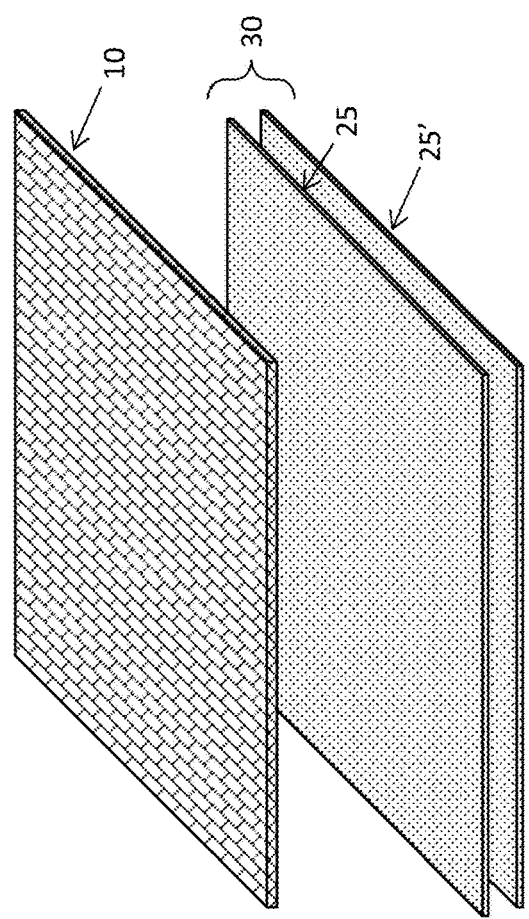
FIG. 11A shows an exploded view of a hernia repair graft including a substrate first layer and an adhesion barrier second layer formed of a plurality (two sheets, in this example) of sheets of ECM.
Figure 12C:
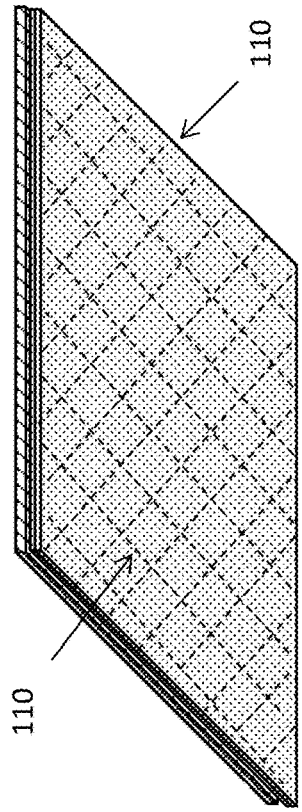
In FIG. 12C the opposite side of the graft (ECM side) is shown, showing the attachment stitching pattern is less dense than the stitching pattern embroidered on the mesh. In any of the grafts herein, an additional adhesion barrier may be attached over the first side as well.
Figure 12B:
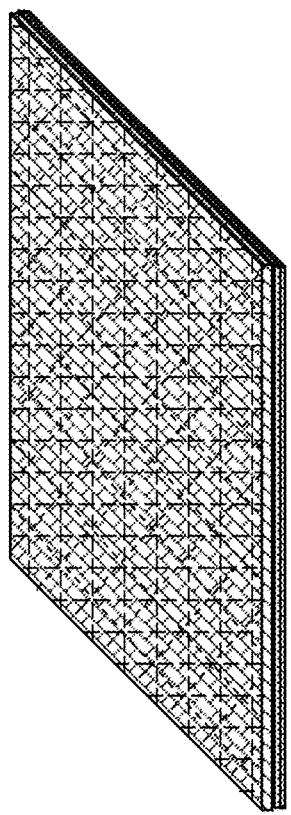
FIG. 12B shows a view of a first side of the graft (embroidered mesh side), showing the layers stacked and attached in a pattern of discrete stitched attachment sites, formed by stitching.
Figure 12A:
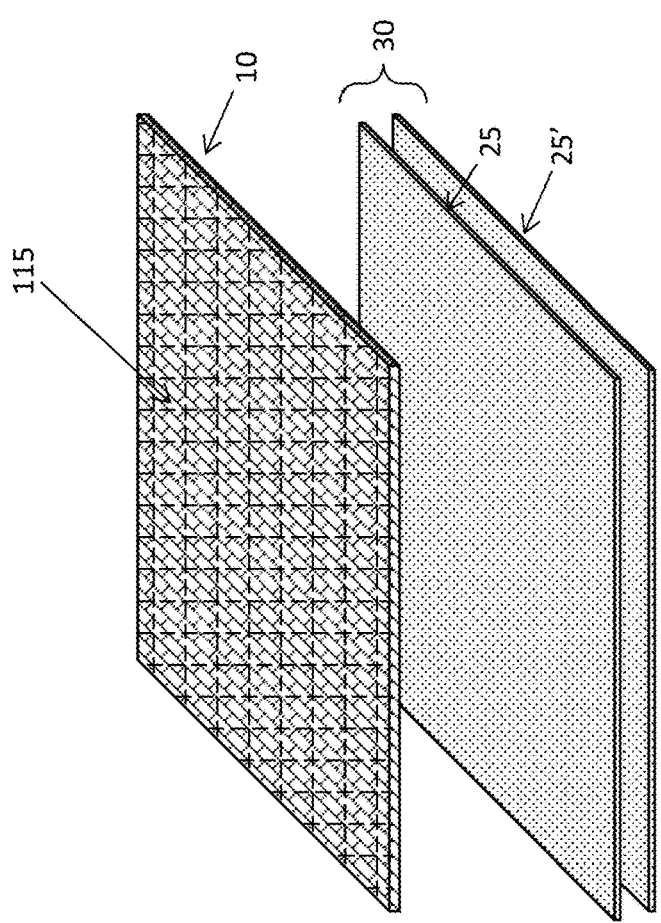
FIG. 12A shows an exploded view of a hernia repair graft including an embroidered substrate first layer and an adhesion barrier second layer formed of a plurality (two sheets, in this example) of sheets of ECM.

FIGS. 11A-C and 12A-C illustrate examples of graft materials having a first layer stacked onto a second layer. The first layer 10 comprises a mesh formed of a non-absorbable material. In FIGS. 12A-12C, the mesh includes a first pattern stitched (embroidered) into the mesh with a bioabsorbable material. In this case, the embroidered pattern does not connect the mesh to another material, but may alter the compliance properties and/or strength of the material, as discussed above. The second layer 30 comprises an anti-adhesive material comprising a plurality of sheets 25, 25' (two are shown) of extracellular matrix material (ECM). The second layer is flexibly attached to the first layer with a second pattern 110 of discrete stitched attachment sites (visible on the back surface of the graft, shown in FIG. 12C). In FIGS. 12A-12C, the second pattern of discrete stitched attachment sites is less dense than the first pattern 115 stitched into the mesh, wherein adjacent discrete attachment sites are separated by a distance of between 0.5 mm and 30 mm and wherein adjacent regions of the first layer and second layer between the discrete attachment sites may slide relative to each other. FIGS. 11B and 12B show the "top" of the grafts, while FIGS. 11C and 12C show the "bottom" (opposite) sides.

Figure 13A:
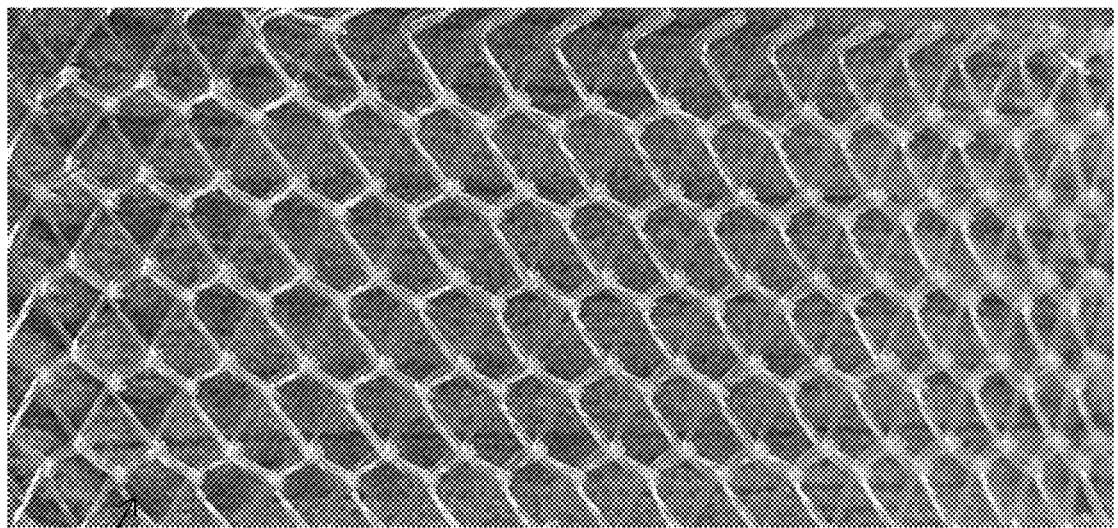
FIG. 13A shows an example of a mesh (substrate) of a hernia repair graft, having an open-cell configuration. This mesh is formed of polypropylene.
Figure 13B:
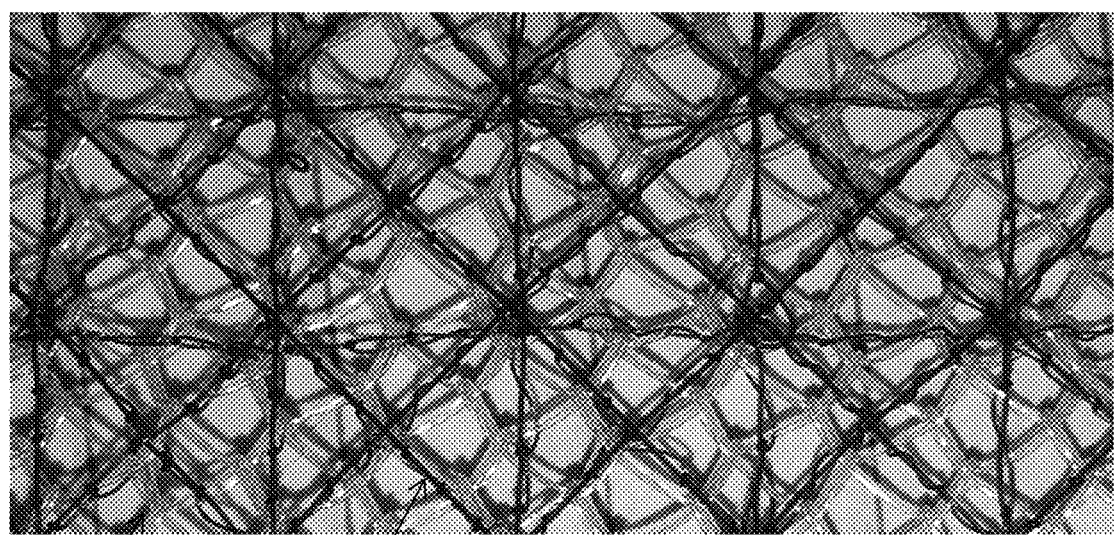
FIG. 13B shows the mesh of FIG. 13A embroidered in a pair of grid sub-patterns with a bioabsorbable material.

FIGS. 13A-13B illustrate a substrate 131 material shown as an open-celled mesh. This this example, the mesh is a polypropylene mesh having an open cell pore of between 0.5 mm and 6 mm diameter. The filaments forming the mesh may have a diameter of between 0.001 inch and 0.010 inches. This mesh may be reinforced with an embroidered pattern of a bioabsorbable material, as shown in FIG. 13B. In this example, the pattern comprises a pair of grid sub-patterns 133 that are rotated at 45° relative offset.

Figure 14A:
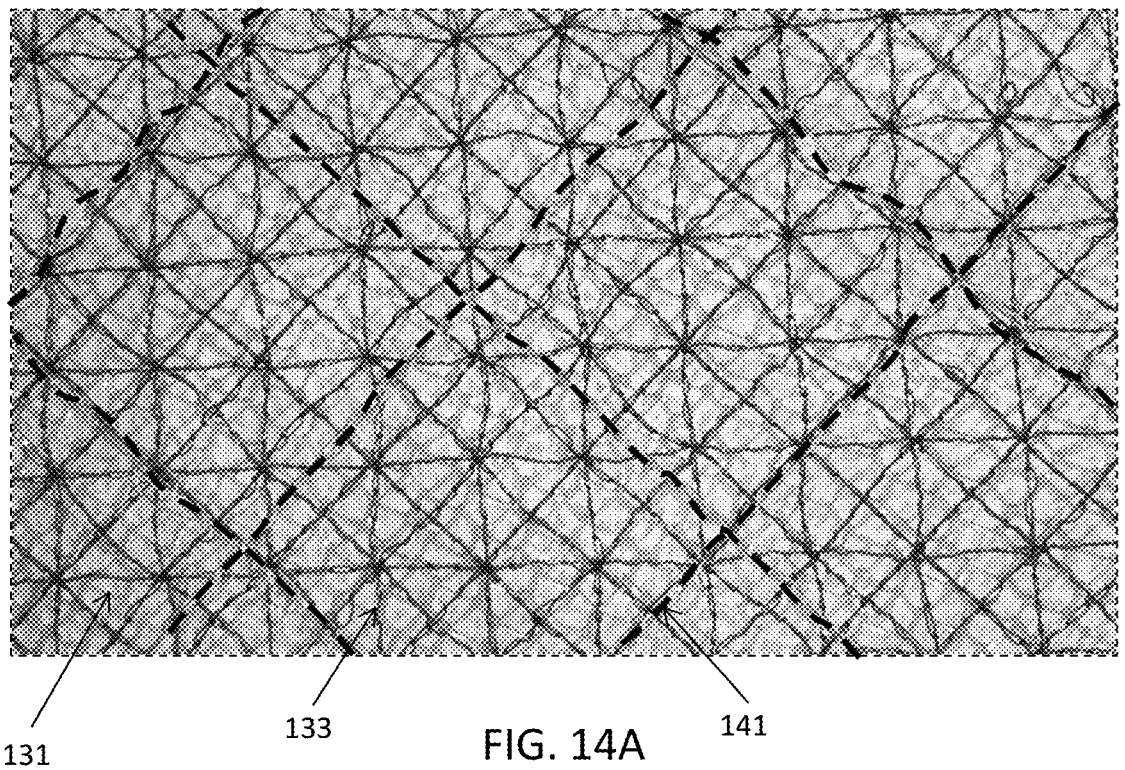
FIG. 14A shows the first side of a hernia repair graft including a mesh, such as the mesh shown in FIGS. 13A-13B, to which an anti-adhesive material (in this example, sheets of ECM) has been sewn.
Figure 14B:
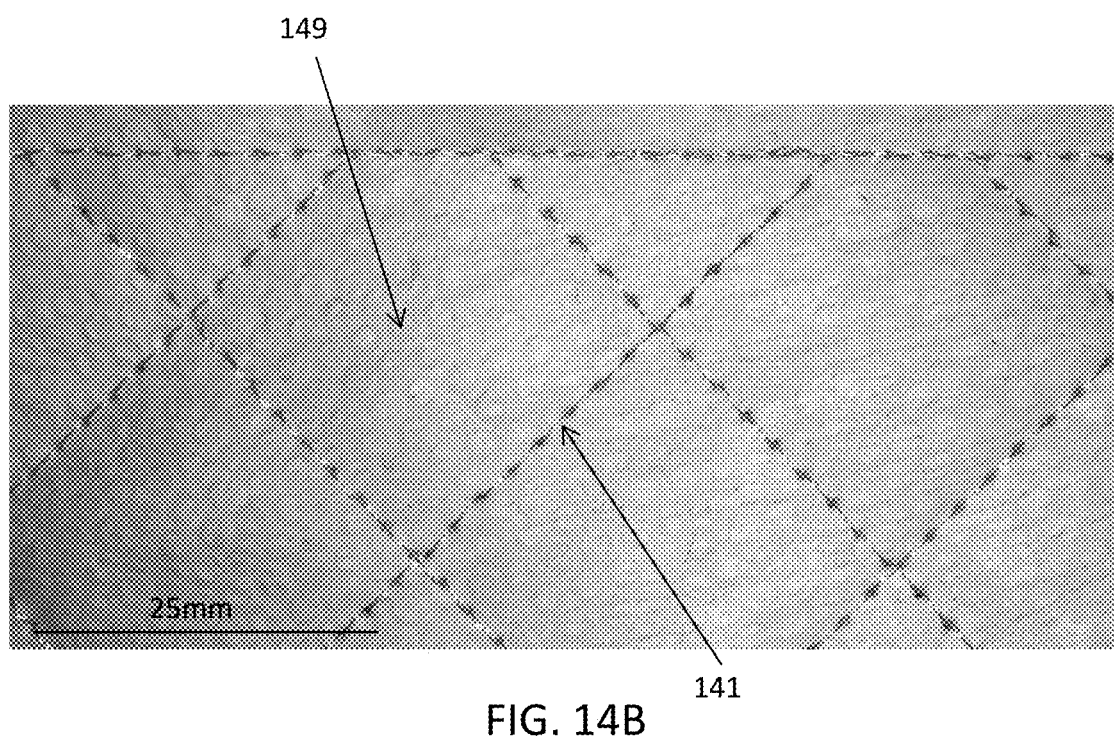
FIG. 14B shows the back side of the hernia repair graft, showing the anti-adhesive material and a stitching pattern attaching the mesh to the anti-adhesive material. This stitching pattern comprises a plurality of discrete attachment sites arranged in the rectangular grid (25 mm×25 mm).

The mesh shown in FIGS. 13A and 13B may be attached via an attachment pattern to an anti-adhesive material as shown in FIGS. 14A-14B. FIG. 14A shows the top or front side of the graft material showing both the mesh 131 with the embroidered pattern 133 as shown in FIGS. 13B, but also shows the attachment pattern of stitches forming the plurality of discrete attachment sites between the two layers. FIG. 14B shows the opposite (back) side of the graft of FIG. 14A, showing the attachment pattern corresponding to the discrete attachment sites sewn to flexibly secure the two layers together. This arrangement of discrete attachment sites does not modify the compliance of the overall material substantially (e.g. less than 15%, less than 13%, less than 11%, less than 10%, etc.), and may allow the two layers to slide relative to each other, particularly in the regions between the attachment sites 149.

Figure 15A:
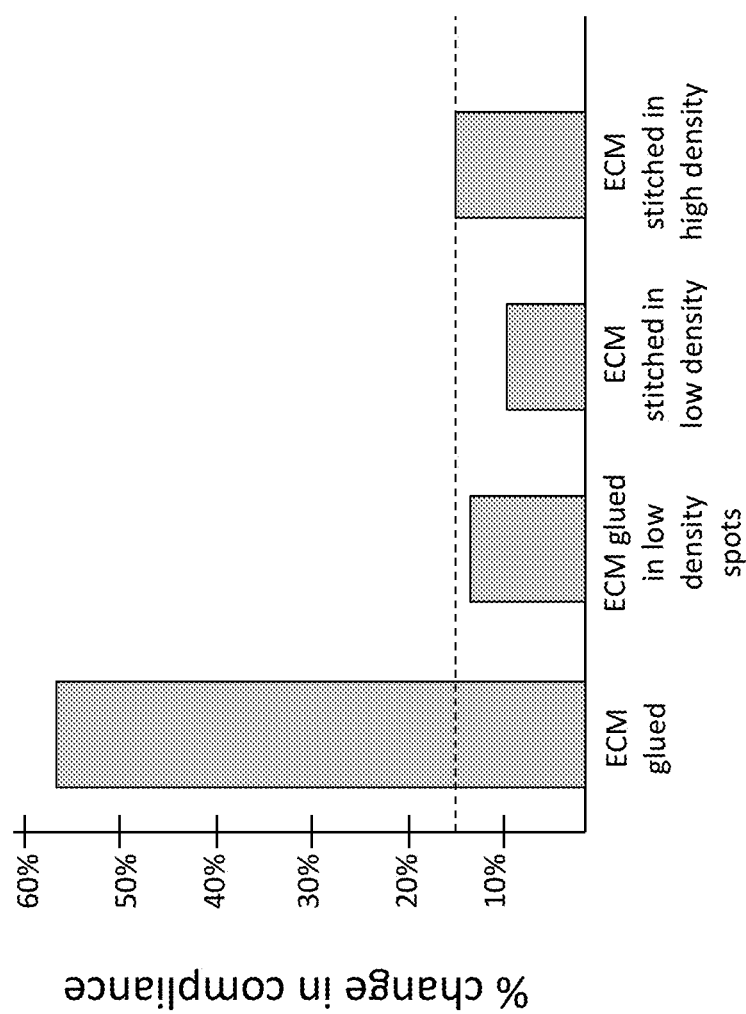
FIG. 15A is a graph showing the percent change in mesh compliance of an unconnected stack of a first embroidered mesh layer and a second ECM layer, under attachment conditions, including gluing the two layers together, gluing with low-density spots (e.g., spots approximately 0.01-0.001 inches separated by an average of approximately 5-20 mm), stitching in low density (e.g., stitches of 0.010 thread separated by an average of 5-20 mm), stitching at high density (e.g., stitches of 0.010 thread separated by an average of 1-5 mm).

As mentioned, the overall compliance of the material may be controlled and may provide advantages compared to other materials, particularly when inserted into the body as a graft. The manner of attachment between the substrate and the anti-adhesion material may be particularly important. In general, it is desirable that the attachment between the two layers does not increase the stiffness (decrease compliance) substantially. For example, in FIG. 15A, the graph shows a comparison between materials having different substrate attached. On the far left, the first bar corresponds to a material in which the substrate (mesh) layer is attached to the anti-adhesion layer (e.g., ECM) by an adhesive or glue. In this case, the overall compliance changes substantially compared to the compliance of either the substrate, the ECM or a loose (unattached) stack of the two, typically >30% (e.g., between 20% and 70%). In contrast, a material in which small, discrete islands ("spots") of adhesive are used to attach the Mesh to the ECM layer (shown in the second bar), the compliance changes less than 15%. A similar result is found with ECM stitched at low density as described herein, and even at relatively higher densities.

Figure 15B:
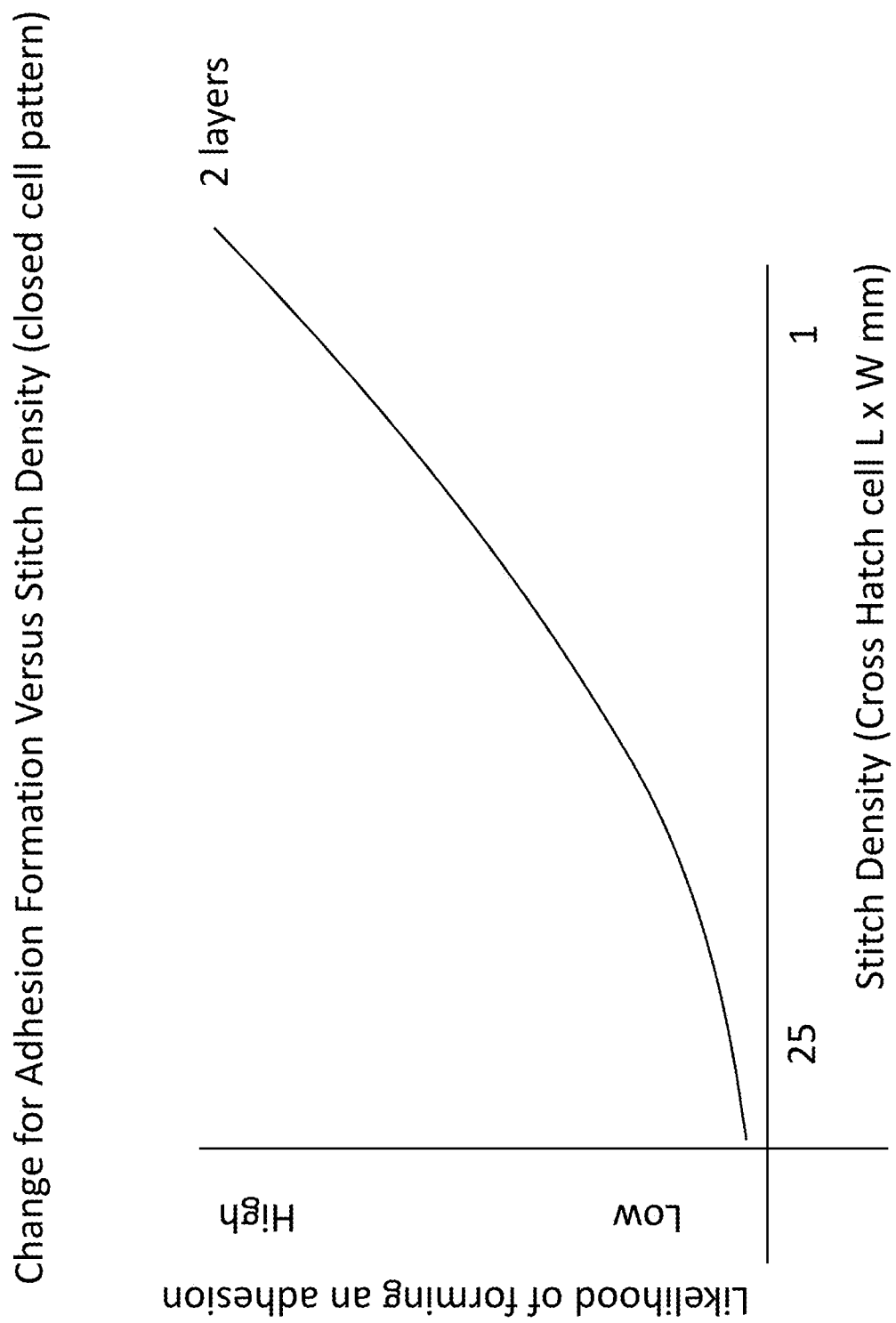
FIG. 15B is a qualitative graph illustrating the change in likelihood of forming adhesions when implanted in the body based on the attachment site density when using a rectangular stitching pattern of 25 to 1 mm L×V. This curve shows the generally increasing trend from low to higher probability of forming an adhesion as the density of the attachment sites (e.g., stitches). In this example, the anti-adhesive material comprises 2 layers of ECM.

In addition, it may also be generally beneficial to reduce the number of attachment sites between the layers, as this may impact adhesion formation to the implant. As shown in FIG. 15B the likelihood of forming an adhesion increases (relatively low to relatively high) as the density of attachment sites increases. In this example, the density corresponds to a stitch density (and may correspond to the amount to exposed thread/polymer material on the surface of the graft). The stitching pattern shown is in a 2-layer (e.g., 2 ECM sheet) embodiment in which the attachment pattern of discrete attachment sites is a stitched grid pattern having grid spacing of between 25 and 1 mm.

Figures 15C, 15D:
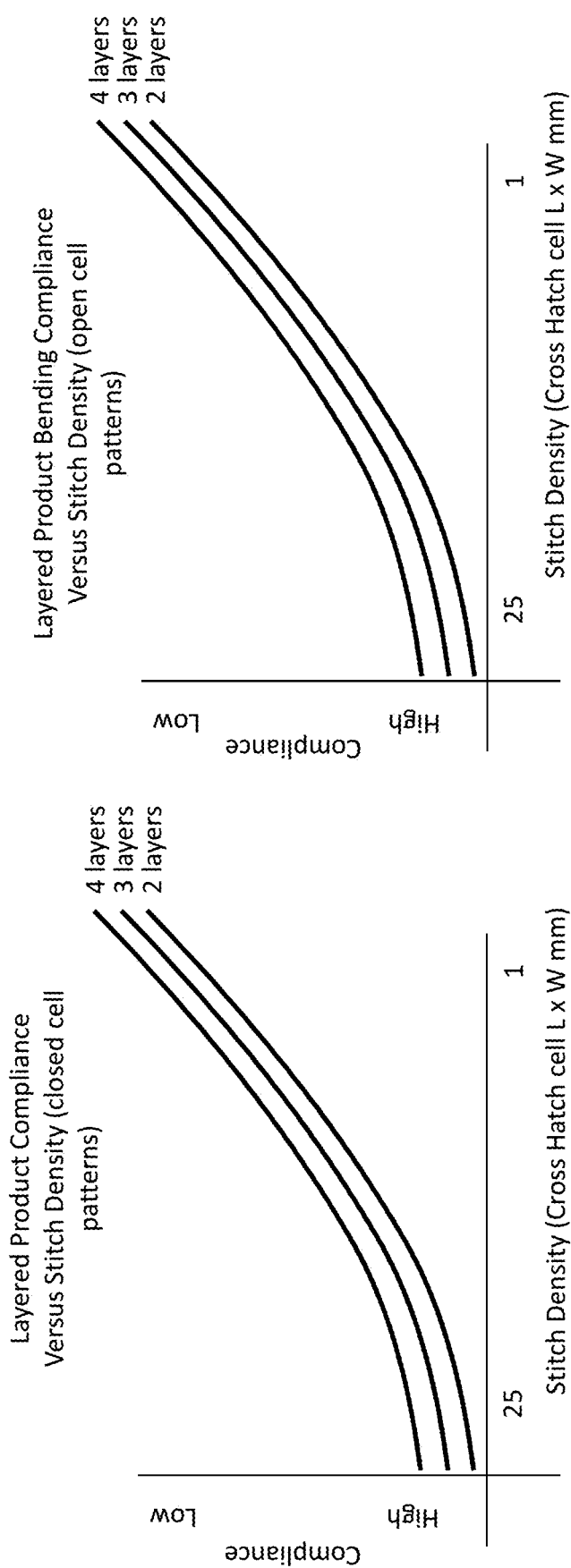
FIGS. 15C and 15D are qualitative graphs illustrating the compliance of the grafts described herein based on their stitch density in which the stitching pattern has a closed cell pattern (FIG. 15C) and an open-cell pattern (FIG. 15D). In general, the less adhesion material (e.g., stitch material or glue material, such as polymer) per unit area between the mesh and the anti-adhesion layers the greater the compliance, although it may reduce the tensile strength. Both figures illustrate that (for layered sheets of anti-adhesion material, e.g., 2, 3, or 4 sheet layers), the compliance decreases as the stitch density increases.

Similarly, FIGS. 15C and 15D illustrate the effect of attachment site density (e.g., stitch density) on compliance for different stitch patterns and different layer numbers of ECM (anti-adhesion material). FIG. 15C shows the relative compliance in layered closed-cell attachment patterns, while FIG. 15D shows a similar relationship in layered open-cell patterns. The closed-cell patterns may also benefit from having increase strength due to the attachment pattern.

Figure 16:
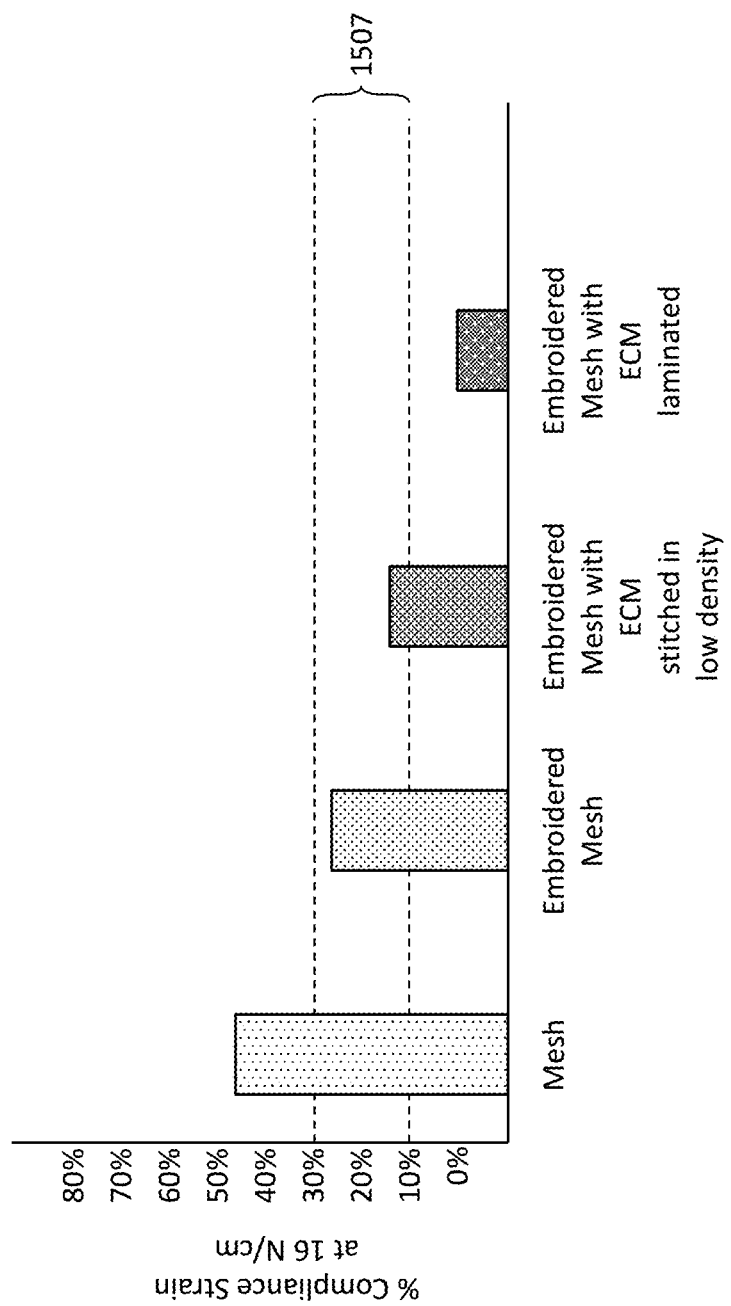
FIG. 16 is a qualitative bar graph showing the percent compliance strain at 16 N/cm for meshes, including those described herein, the same meshes when embroidered, e.g., with a bioabsorbable material, embroidered meshes stitched to ECM as described herein, and embroidered meshes the ECM laminated.

In any of these apparatuses (e.g., grafts) described herein, it may be particularly beneficial to match the compliance properties of the material to the body, especially at implantation time. Over time in the body, this compliance may change (preferably increase) to prevent stiffening and discomfort due to compliance increase as the implant becomes ingrown and/or scarred. FIG. 16 illustrates the percent compliance strain at 16 N/cm of the mesh alone (far left), the embroidered mesh, the embroidered mesh with ECM stitched at low density, and an embroidered mesh with ECM laminated on. It is desirable, based on clinical and experimental data, to have the percent compliance strain at 16 N/cm be between 10% and 30% 157, at least at implantation. As indicated the meshes described herein (and particularly the embroidered mesh with ECM stitched at low density) is within this desired compliance window, in contrast to variations in which the anti-adhesion material is laminated or attached at high density.

As used herein, "inhibiting" includes reducing, decreasing, blocking, preventing, delaying, stopping, and/or down regulating. By way of example, but not of limitation, inhibiting adhesions includes reducing adhesion formation.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A hernia repair graft comprising:
a first layer stacked onto a second layer;
wherein the first layer comprises:
  a mesh and a first pattern embroidered into the mesh;
  wherein the second layer comprises a sheet of anti-adhesive material comprising a medical textile material;
further wherein the second layer is flexibly attached to the first layer with a plurality of discrete attachment sites, wherein adjacent regions of the first layer and second layer between the discrete attachment sites may slide relative to each other.

2. The hernia repair graft of claim 1, wherein the medical textile comprises an extracellular matrix (ECM) material.

3. The hernia repair graft of claim 1, wherein the mesh comprises a knitted mesh.

4. The hernia repair graft of claim 1, wherein the mesh comprises polypropylene.

5. The hernia repair graft of claim 1, wherein the mesh comprises polytetrafluoroethylene (PTFE), nylon or polyester.

6. The hernia repair graft of claim 1, wherein the mesh has open cell pore of between 0.5 mm and 6 mm diameter.

7. The hernia repair graft of claim 1, wherein the mesh is formed of a warp knitted filament having a diameter of between 0.001 inch and 0.010 inches.

8. The hernia repair graft of claim 1, wherein the mesh is formed of a warp knitted filament having a diameter of between 0.003 inch and 0.006 inches.

9. The hernia repair graft of claim 1, wherein the mesh is formed of a plurality of fibers that are knitted together.

10. The hernia repair graft of claim 1, wherein the first pattern comprises adjacent lines of stitching that cross to interlock at regular intervals.

11. The hernia repair graft of claim 1, wherein the first pattern comprises a first stitching sub-pattern and a second stitching sub-pattern, wherein the first stitching sub-pattern overlaps with the second stitching sub-pattern and the first stitching sub-pattern is rotated between 25 and 65 degrees relative to the second stitching sub-pattern.

12. The hernia repair graft of claim 1, wherein the sheet of anti-adhesive material comprises a sheet of extracellular matrix derived from one or more of a dermis, pericardium, peritoneum, intestine, stomach, or forestomach.

13. The hernia repair graft of claim 1, wherein the second layer further comprises a plurality of stacked sheets of the extracellular matrix (ECM) material.

14. The hernia repair graft of claim 1, wherein the discrete attachment sites comprise a second stitching pattern.

15. The hernia repair graft of claim 1, wherein the discrete attachment sites comprise a second stitching pattern, wherein the second stitching pattern comprises a grid pattern.

16. The hernia repair graft of claim 1, wherein adjacent discrete attachment sites are separated by a distance of between 0.5 mm and 30 mm.

17. The hernia repair graft of claim 1, wherein the second layer is flexibly attached to the first layer with a second pattern formed of the discrete attachment sites having a density of attachment sites that is less than about 10 attachments/mm$^2$.

18. A hernia repair graft comprising:
a first layer stacked onto a second layer;
wherein the first layer comprises:
 a mesh and a first pattern embroidered into the mesh;
wherein the second layer comprises a sheet of anti-adhesive material comprising a biotextile material;
further wherein the second layer is flexibly attached to the first layer with a plurality of discrete attachment sites, wherein adjacent regions of the first layer and second layer between the discrete attachment sites are unattached to each other;
further wherein the first pattern does not extend into the second layer.

19. A hernia repair graft comprising:
a first layer stacked onto a second layer;
wherein the first layer comprises: a mesh formed of a non-absorbable material and a first pattern stitched into the mesh with a bioabsorbable material;
wherein the second layer comprises a biotextile and medical textile material;
further wherein the second layer is flexibly attached to the first layer with discrete attachment sites, wherein the discrete attachment sites are distributed in a pattern that is less dense than the first pattern stitched into the mesh, and wherein adjacent regions of the first layer and second layer between the discrete attachment sites are unattached to each other.

* * * * *